US007142987B2

(12) United States Patent
Eggers

(10) Patent No.: US 7,142,987 B2
(45) Date of Patent: Nov. 28, 2006

(54) APPARATUS, SYSTEM, AND METHOD OF ARCHIVAL AND RETRIEVAL OF SAMPLES

(75) Inventor: Mitchell D. Eggers, Carlsbad, CA (US)

(73) Assignee: Genvault Corporation, Carlsbad, CA (US)

( * ) Notice: Subject to any disclaimer, the term of this patent is extended or adjusted under 35 U.S.C. 154(b) by 652 days.

(21) Appl. No.: 10/005,529

(22) Filed: Nov. 7, 2001

(65) Prior Publication Data

US 2003/0087446 A1 May 8, 2003

(51) Int. Cl.
*G01N 33/48* (2006.01)
*G01N 33/50* (2006.01)
*G01N 31/00* (2006.01)
*G06F 19/00* (2006.01)
*G05B 21/00* (2006.01)

(52) U.S. Cl. ............... 702/19; 422/50; 422/62; 422/63; 422/64; 422/65; 422/66; 422/67; 422/68.1; 422/81; 422/82; 422/99; 422/82.05; 436/43; 436/48; 436/174; 700/266; 700/275; 702/1; 702/20; 702/21; 702/22; 702/23; 702/27; 702/30; 702/31; 702/32

(58) Field of Classification Search ............... 422/50, 422/62, 63, 64, 65, 66, 67, 68.1, 81, 82, 99, 422/82.05; 436/43, 48, 174; 700/266, 275; 702/1, 19, 20, 21, 22, 23, 27, 30, 31, 32
See application file for complete search history.

(56) References Cited

U.S. PATENT DOCUMENTS

| | | | |
|---|---|---|---|
| 4,684,613 A | 8/1987 | Barrere | 435/301 |
| 4,896,024 A | 1/1990 | Morello | 235/381 |
| 5,125,240 A | 6/1992 | Knippscheer | 62/266 |
| 5,139,744 A | 8/1992 | Kowalski | 422/67 |
| 5,355,304 A | 10/1994 | DeMoranville | 364/413.02 |

(Continued)

FOREIGN PATENT DOCUMENTS

WO    WO 01/31317    5/2001

(Continued)

OTHER PUBLICATIONS

Elliot, J.C., Bowen, K.L., Walker, T., Sauve, V.M., and Fourney, R.M.: "Extration of DNA from FTA Blood Stain Collection Cards for Construction of a Large STR National DNA Data Base;" 8th International Symposium on Human ID, 1997.

(Continued)

*Primary Examiner*—Jill Warden
*Assistant Examiner*—Brian Sines
(74) *Attorney, Agent, or Firm*—Pillsbury Winthrop Shaw Pittman LLP

(57) ABSTRACT

A sample archive method and system implement a plurality of sample carriers configured to support a plurality of sample nodes in a predetermined spatial relationship, sample storage devices for selectively placing the plurality of sample carriers in an archive, and sample node removal apparatus for locating and removing selected ones of the plurality of sample nodes. Alternative embodiments are disclosed wherein the sample node removal apparatus comprises a laser and a mechanical clipping tool, which may be manually operated or automated. An optical component may be operative to detect the location of selected sample carriers in the archive, selected ones of the plurality of sample nodes, or both. A positioning component may position the sample node removal apparatus responsive to signals transmitted by the optical component. Various apparatus and methods of archiving samples and preparing the same for analysis are also disclosed.

36 Claims, 10 Drawing Sheets

U.S. PATENT DOCUMENTS

| | | | | |
|---|---|---|---|---|
| 5,366,896 | A | 11/1994 | Margrey | 436/48 |
| 5,411,893 | A | 5/1995 | Eden | 436/165 |
| 5,441,698 | A | 8/1995 | Norell | 422/58 |
| 5,445,294 | A | 8/1995 | Gardner | 221/1 |
| 5,460,057 | A | 10/1995 | Ostrup | 73/864.81 |
| 5,516,487 | A * | 5/1996 | Rosenthal et al. | 422/55 |
| 5,638,170 | A | 6/1997 | Trinka | 356/244 |
| 5,800,777 | A | 9/1998 | Jehan | 422/63 |
| 5,805,456 | A | 9/1998 | Higham | 364/479.06 |
| 5,841,975 | A | 11/1998 | Layne | 395/200.33 |
| 6,103,518 | A | 8/2000 | Leighton | 435/286.3 |
| 6,108,588 | A | 8/2000 | McGrady | 700/231 |
| 6,127,928 | A * | 10/2000 | Issacman et al. | 340/572.1 |
| 6,362,737 | B1 * | 3/2002 | Rodgers et al. | 340/572.1 |
| 6,699,710 | B1 * | 3/2004 | Kononen et al. | 435/283.1 |

FOREIGN PATENT DOCUMENTS

| | | |
|---|---|---|
| WO | WO 01/31333 | 5/2001 |

OTHER PUBLICATIONS

Bever, R., Jarvis, D., DiPerro, D., and McElfresh K.; "Implementation of Laboratory Automation for the Analysis of STR Loci;" 8th International Symposium on Human ID, 1997.

Belgrader, P., and Marino, M.A.; Coupled DNA Purification and PCR Amplification of STR Loc i from Bloodstain Cards Using a Robotic System; BioTechniques, 19:427-432, 1995.

Hansen, P., and Blakesley R.: "Sample Archiving of Bacterial and Plasmid DNAs for Future Use;" Focus, vol. 20, No. 3, pp. 72-74, 1998.

* cited by examiner

APPARATUS, SYSTEM, AND METHOD OF ARCHIVAL AND RETRIEVAL OF SAMPLES

The present application is related to non-provisional application Ser. No. 10/007,355, filed Nov. 7, 2001, entitled "SAMPLE CARRIER" and also to non-provisional application Ser. No. 10/005,415, filed Nov. 7, 2001, entitled "ARCHIVE AND ANALYSIS SYSTEM AND METHOD" the disclosures of which are hereby incorporated by reference in their entirety.

FIELD OF THE INVENTION

Aspects of the present invention relate generally to archival of sample material, and more particularly to a system and method of archiving and retrieving biological or non-biological samples maintained in desiccated form at a plurality of sample nodes on a carrier.

DESCRIPTION OF THE RELATED ART

In many applications such as pharmaceutical and medical research, law enforcement, and military identification, for example, it is often desirable to have access to numerous biological samples. Conventional biorepositories or other sample storage facilities utilize liquid or low temperature cryogenic systems for sample storage; these liquid and cryogenic systems are expensive both to create and to maintain. Additionally, current technology generally presents system operators with complicated and labor intensive maintenance and administrative responsibilities.

Specifically, the intricacies of cryogenic systems may typically oblige technicians, researchers, and system operators to engage in coordinated labor for weeks to retrieve and to prepare thousands of deoxyribonucleic acid (DNA) samples from whole blood. Accordingly, conventional approaches for archiving DNA in liquid or cryogenic states are fundamentally inadequate to the extent that they do not accommodate high volume processing and sample throughput. Current research trends recognize benefits associated with systems and methods of archiving and retrieving biological and non-biological samples which may be capable of processing thousands of samples per day; current technology, however, is inadequate to attain throughput at this level. In fact, current systems and methods cannot attain processing throughput of one hundred or more samples per day.

Although some small volume liquid-state DNA and blood archival techniques have been useful in the past, present methodologies are not capable of supporting the increasing storage and retrieval rates required as advancing genomics technology becomes more prevalent as a research and diagnostic tool. Since the traditional cryogenic-based archival format is difficult and expensive to automate, systems based upon existing technology are generally not amenable to the high throughput demands of the market.

Recently, biological research laboratory systems have been proposed which incorporate archiving and retrieval of blood samples in dry or desiccated form. Present systems are generally based upon modifications or variations of known techniques for storing DNA or other organic samples on a suitable substrate such as filter paper; some systems require, or substantially benefit from, soaking the substrate or paper with chemical denaturants and detergents prior to use. In any event, however, existing desiccated sample archival systems are manually operated or only partially automated, and hence do not meet the high volume processing demands of the market. Additionally, these systems employ a mechanical punch or other tool which is operative to remove samples from substrates, typically by punching through or otherwise physically engaging the substrate material. Consequently, these tools necessarily make contact with multiple samples during ordinary use.

In that regard, those of skill in the art will appreciate that even if the current substrate-based archive systems were fully automated, significant cross contamination problems would undoubtedly remain. During the sample removal punching process, extraneous fibers adhere to the punching tool or are otherwise released from the substrate, contaminating subsequent samples handled by the tool. These contamination problems limit both the utility and the practicality of traditional technologies. Moreover, the density of the storage facility is ultimately limited by the inherent saturation limit of the substrate, as well as by the precision of mechanical and robotic components of the system.

In particular, full automation of the storage and retrieval processes in systems employing conventional filter paper or substrate card formats would necessarily require very precise robotics and other machinery operating repeatedly to identify, to retrieve, and to replace individual storage cards within a large volume storage room or vault. Although precise, high-resolution robotic systems are currently available, finely tuned precision is achieved only when the mechanisms are operated within a small area. Accordingly, automating the storage and retrieval process for filter paper card or other substrate-based archival systems within an entire large scale vault is not a practical solution given current mechanical and robotic limitations.

SUMMARY

Embodiments of the present invention overcome various shortcomings of conventional technology, providing a system and method of automated archival and retrieval of desiccated biological or non-biological samples. In accordance with one aspect of the invention, for example, a fully automated desiccated sample storage system may be operative to achieve very high storage and retrieval rates, for example, greater than one hundred samples per day. An archive management system may include or support some or all of the following, inter alia: patient consenting; questionnaire transcription; blood deposition; sample bar coding; archive storage; electronic sample browsing; sample retrieval; sample purification and extraction; and sample packaging and shipping. Coupled with the internet or other wide-area or local network, a fully automated archive facility may accommodate efficient search and timely transport of biological or other samples, as well as attendant data and other information, throughout the world.

As set forth in detail below, the foregoing system and method may employ a desiccated sample carrier configured and operative to facilitate efficient and timely access to contamination-free samples. In accordance with this aspect of the present invention, a sample carrier may accommodate very high sample densities at room temperature. Consequently, archive density may be satisfactory for high throughput demands, while the expense and complications associated with cryogenic or liquid sample storage facilities may be reduced or eliminated.

In accordance with one aspect of the present invention, for example, a sample carrier comprises a structural array and a plurality of sample nodes; each of the plurality of sample nodes being removably attached to the structural array at a respective attachment point and operative to carry a discrete sample. In some embodiments, each of the plurality of sample nodes is operative to carry a biological sample, including proteins, polynucleotides, and DNA; in some alternative embodiments, each of the plurality of sample nodes is operative to carry a non-biological sample.

In accordance with another aspect of the present invention, the sample carrier further comprises identifying indicia, some of which are decipherable by an optical sensor. In some embodiments, each of the plurality of sample nodes comprises an associated transceiver operative to transmit a unique signal; additionally, the associated transceiver may be operative to receive a control signal from a remote device.

Depending upon, inter alia, the type of sample and overall system requirements of the various embodiments, each of the plurality of sample nodes is solid or porous. Sample carrier embodiments are disclosed wherein each of the plurality of sample nodes comprises a sample support medium, which may comprise cellulose, a polymer such as polystyrene, or other material. In accordance with some embodiments, the sample support medium is derivatized, and may be positively charged or negatively charged.

In another embodiment a sample carrier comprises a plurality of structural arrays supported in a predetermined spatial relationship and a plurality of sample nodes, wherein each of the plurality of sample nodes is removably attached to one of the plurality of structural arrays at a respective attachment point and operative to carry a discrete sample. An alternative is disclosed wherein each of the plurality of structural arrays is supported in a predetermined spatial relationship relative to a respective sample container, such as a respective well of a multi-well plate.

In the foregoing embodiment employing a plurality of structural arrays, all of the alternatives and features mentioned above with reference to the single structural array embodiment are incorporated.

In accordance with another aspect of the present invention, a method of transferring a specimen to a sample carrier comprises providing a sample carrier comprising a structural array supporting a plurality of sample nodes, and contacting the plurality of sample nodes to the specimen. Various alternatives are disclosed wherein the specimen is solid, gaseous, and liquid in form.

In some embodiments, the method further comprises selectively applying a preservative to the plurality of sample nodes subsequent to the contacting; it may be desirable that the preservative is operative to desiccate the specimen transferred to the plurality of sample nodes.

The method may further comprise washing the plurality of sample nodes subsequent to the contacting. Additionally or alternatively, as noted above, the method may further comprise allowing the plurality of sample nodes to desiccate subsequent to the contacting, with or without the assistance of a preservative.

In accordance with another aspect of the present invention, a method of transferring specimens to a sample carrier comprises providing a sample carrier comprising a plurality of structural arrays, each of the plurality of structural arrays being supported in a predetermined spatial relationship relative to a respective specimen container and supporting a plurality of sample nodes, and contacting the plurality of sample nodes supported by selected ones of the plurality of structural arrays to a respective specimen. In some embodiments, the contacting comprises bringing the plurality of sample nodes supported by each of the plurality of structural arrays into contact with a specimen in the respective specimen container.

In the foregoing embodiment employing a plurality of structural arrays, all of the alternatives and features mentioned above with reference to the single structural array embodiment are incorporated.

In some embodiments, a sample carrier comprises: a structural array comprising a plurality of sample nodes, wherein each of the plurality of sample nodes is removably attached to the structural array at a respective attachment point and comprises a discrete sample support medium; and a specimen carried by the sample support medium at one or more of the plurality of sample nodes.

In some embodiments, the specimen is biological, including proteins, polynucleotides, and DNA; in some alternative embodiments, the specimen is non-biological.

Depending upon, inter alia, the type of sample and overall system requirements of the various embodiments, the sample support medium is solid or porous. Sample carrier embodiments are disclosed wherein the sample support medium comprises cellulose, a polymer such as polystyrene, or other material. In accordance with some embodiments, the sample support medium is derivatized or treated with a chemical compound, and may be positively charged or negatively charged.

In accordance with another aspect of the invention, a sample archive system comprises a plurality of sample carriers configured to support a plurality of sample nodes in a predetermined spatial relationship, sample storage means for selectively placing the plurality of sample carriers in an archive, and sample node removal means for locating and removing selected ones of the plurality of sample nodes. Alternative embodiments are disclosed wherein the sample node removal means comprises a laser and a mechanical clipping tool.

In some embodiments, the system comprises an optical component operative to detect the location of the selected ones of the plurality of sample nodes; it may be desirable that such a system further comprises a positioning component operative to position the sample node removal means responsive to signals transmitted by the optical component.

In some embodiments, a sample archive system comprises a plurality of sample carrier receptacles, each of the plurality of sample carrier receptacles configured to receive one or more sample carriers supporting a plurality of sample nodes, a sample carrier storage device operative to place selected ones of the one or more sample carriers in selected ones of the plurality of sample carrier receptacles, a sample carrier location device operative to locate the selected ones of the one or more sample carriers, a sample carrier retrieval device operative to retrieve the selected ones of the one or more sample carriers from ones of the plurality of sample carrier receptacles, and sample node removal means for identifying and removing selected ones of the plurality of sample nodes.

In some embodiments, at least a portion of the plurality of sample carrier receptacles includes a rack, while in other embodiments, at least a portion of the plurality of sample carrier receptacles includes a drawer. Embodiments of the system are disclosed wherein the sample carrier location device is a bar code reader. Additionally or alternatively, embodiments of the system are disclosed wherein the sample node removal means comprises a laser and a mechanical clipping tool.

A system is disclosed wherein the sample node removal means further comprises an optical component operative to detect the location of the selected ones of the plurality of sample nodes; in some embodiments, the sample node removal means may further comprise a positioning component operative to position a laser responsive to signals transmitted by the optical component.

In some embodiments, it may be desirable that the system further comprise means for processing a sample supported by the selected ones of the plurality of sample nodes, or a controller for controlling operation of the sample carrier storage device and the sample carrier retrieval device.

In accordance with a further aspect of the present invention, a sample archive system comprises an archive comprising a plurality of sample carrier receptacles, each of the plurality of sample carrier receptacles configured to receive one or more sample carriers supporting a plurality of sample nodes, and a robotics system comprising mechanisms operative to store and to retrieve selected ones of the one or more sample carriers from the archive. The foregoing system may comprise a sample carrier locator coupled to the robotics system and operative to detect a location of the selected ones of the one or more sample carriers.

In some embodiments of the system, the sample carrier locator comprises an optical sensor; a system is further disclosed wherein the robotics system is automatically responsive to signals from the sample carrier locator. As noted above, a system may further comprise a sample node removal device operative to identify and to remove selected ones of the plurality of sample nodes from selected ones of the one or more sample carriers. A sample node locator coupled to the sample node removal device may be operative to detect a location of the selected ones of the plurality of sample nodes. Embodiments are disclosed wherein the sample node removal device is automatically responsive to signals from the sample node locator, which may comprise an optical sensor or a respective transceiver incorporated in each of the plurality of sample nodes. The system may include a sample carrier locator embodied in a bar code reader.

In some systems, the sample node removal device comprises a mechanical clipping tool and a mechanical positioning system to position the mechanical clipping tool relative to the selected ones of the plurality of sample nodes, whereas in other systems, the sample node removal device comprises a laser and a mechanical positioning system to position the laser relative to the selected ones of the plurality of sample nodes. Embodiments are disclosed wherein the mechanical positioning system is operative to position the clipping tool or the laser responsive to signals transmitted by an optical sensor. As noted above, such systems may further comprise means for processing a sample supported by the selected ones of the plurality of sample nodes. In some alternative embodiments, the system further comprises a computer operative to control the robotics system and the sample node removal device.

In accordance with still another aspect of the present invention, a method of archiving samples comprises selectively transferring a specimen to a plurality of discrete sample nodes attached to a sample carrier, archiving the sample carrier in an archive facility, and recording the location of the sample carrier in the archive facility. Embodiments of the foregoing method further comprise washing the plurality of discrete sample nodes subsequent to the selectively transferring, while other embodiments additionally or alternatively comprise assigning identifying indicia, such as a bar code, for the sample carrier in accordance with the recording. The recording may comprise writing data records associated with the plurality of discrete sample nodes to a computer readable data storage medium.

Another method of archiving samples comprises obtaining a specimen from a source, associating an identifier to the source and to the specimen, writing the identifier and information associated with the source and the specimen to a data structure, selectively transferring the specimen to a plurality of discrete sample nodes attached to a sample carrier and placing the sample carrier in a sample carrier receptacle at an archive facility. The foregoing method may further comprise recording the location of the sample carrier in the archive facility; additionally or alternatively, the method may further comprise acquiring consent to obtain the specimen.

In some embodiments, the method comprises assigning identifying indicia, such as a bar code, for the sample carrier in accordance with the associating and the selectively transferring. As noted above, the recording may comprise writing data records associated with the plurality of discrete sample nodes to a computer readable data storage medium.

A computer readable medium is disclosed which is encoded with data and computer executable instructions; the data and instructions causing an apparatus executing the instructions to: receive information regarding a sample and a source of the sample; assign an identifier to the sample, the source, and the information; record the identifier and the information in a data structure; and record the location within a sample carrier of each of a plurality of discrete sample nodes supporting the sample.

The computer readable medium may further cause an apparatus to transmit control signals to a remote device at an archive facility. Additionally or alternatively, some embodiments of the computer readable medium further cause an apparatus to transmit control signals to a sample node removal device operative to locate and to remove selected ones of the plurality of discrete sample nodes, or to transmit control signals to a sample carrier storage device operative to place selected ones of a plurality of sample carriers in an archive. In the latter embodiment, the computer readable medium may additionally cause an apparatus to transmit control signals to a sample carrier retrieval device operative to retrieve the selected ones of the plurality of sample carriers from the archive.

In accordance with one aspect of the present invention, a method of preparing an archive sample for analysis comprises identifying a sample to be analyzed, responsive to the identifying, ascertaining a location of the sample on a discrete sample node supported by a sample carrier, responsive to the ascertaining, removing the discrete sample node from the sample carrier, and preparing the sample for analysis.

Embodiments of the foregoing method are disclosed wherein the identifying comprises interrogating a data structure such as a database. In some embodiments, the ascertaining comprises utilizing an optical sensor, which may include reading a bar code. Alternatively, the ascertaining comprises identifying a unique signal transmitted from a transceiver attached to the discrete sample node; in this embodiment, the removing may comprise transmitting a control signal to the transceiver.

As in the embodiments described above, methods are disclosed wherein the removing comprises utilizing a laser or a mechanical clipping tool. The preparing may comprise depositing the discrete sample node in a sample container; additionally or alternatively, the preparing may comprise washing sample material attached to the discrete sample node.

In the foregoing method, the composition of the sample (i.e. non-biological, biological, etc.) is as described above; accordingly, the method may further comprise amplifying a polynucleotide.

In some embodiments, a method of preparing an archive sample for analysis comprises receiving a request related to an experiment, identifying a sample suitable for the experiment, responsive to the receiving and the identifying, locating a sample carrier supporting the sample on a discrete sample node, detecting a location of the discrete sample node on the sample carrier, removing the discrete sample node from the sample carrier, and preparing the sample for analysis. As noted above, the locating may comprise any or all of the following: interrogating a database maintaining records related to the sample carrier; utilizing an optical sensor; and reading a bar code.

In accordance with one aspect of the method, the detecting comprises obtaining video signals output from an optical sensor; accordingly, the removing may comprise automatically or manually operating a sample node removal device responsive to the obtaining video signals. Additionally or alternatively, the detecting comprises identifying a unique signal transmitted from a transceiver attached to the discrete sample node; in this embodiment, the removing may comprise transmitting a control signal to said transceiver.

In another embodiment, a sample node removal system comprises a sample carrier configured to support a plurality of sample nodes in a predetermined spatial relationship, and node removal means for locating and removing selected ones of said plurality of sample nodes. The node removal means may be embodied in the hardware, such as a laser or a mechanical clipping tool, and computerized elements described above. An optical component may be operative to detect the location of the selected ones of the plurality of sample nodes; in some embodiments, signals output from the optical component may be used in conjunction with a positioning component operative to position the node removal means responsive to signals transmitted by said optical component. As noted above, such a system may further comprise a computer operative to receive the signals and to control the positioning component and the node removal means.

In another embodiment, a method of preparing an archive sample for analysis comprises identifying a sample to be analyzed, responsive to the identifying, obtaining the sample, preparing the sample for analysis, and selectively repeating the identifying, the obtaining, and the preparing at a rate sufficient to prepare in excess of 100 samples for analysis per day. As noted above, the identifying may comprise interrogating a database, utilizing an optical sensor, or both. The obtaining may comprise automatically or manually operating a sample node removal device, which may be a laser or a mechanical clipping tool.

Aspects of the methods previously discussed may be incorporated into the foregoing embodiment. Additionally, the selectively repeating may occur at a rate sufficient to prepare in excess of 200 samples for analysis per day; methods are disclosed wherein the selectively repeating occurs at a rate sufficient to prepare in excess of 500 samples for analysis per day.

In some embodiments, a method of providing biological analyses to a remote client comprises maintaining a sample archive comprising a plurality of discrete sample nodes, receiving a request for a biological analysis from a remote client, the request comprising identification of a selected sample node from the plurality of discrete sample nodes and identification of a selected assay, responsive to the receiving, retrieving the selected sample node from the archive and preparing the selected assay, and performing the selected assay for the selected sample node.

The method of providing biological analyses may further comprise transmitting results of the performing and data representative of the performing to the remote client; the transmitting may include encrypting the results and the data. In some embodiments, the method may additionally comprise shipping the selected sample node to the remote client. The request may be received via a network connection.

Embodiments of the foregoing method are disclosed wherein the assay is a genomics experiment or a proteomics experiment, for example, and wherein the retrieving the selected sample node comprises some or all of the following: interrogating a database; utilizing an optical sensor; and automatically or manually operating a sample node removal device, which may comprise a laser or a mechanical clipping tool. As with the methods previously described, a method of providing biological analyses may further comprise washing the sample prior to the performing.

In accordance with another aspect of the invention, a method of providing samples to a remote client comprises maintaining a sample archive comprising a plurality of discrete sample nodes, receiving a request, via a network connection or otherwise, for a sample from a remote client, responsive to the receiving, identifying a selected one of the plurality of discrete sample nodes in the archive, the selected one of the plurality of discrete sample nodes carrying the sample, retrieving the selected one of the plurality of sample nodes from the archive, and shipping the selected one of the plurality of sample nodes to the remote client.

In some embodiments, the method may further comprise performing an analysis of the sample prior to the shipping, and may additionally comprise transmitting results of the performing and data representative of the performing to the remote client. The above-mentioned shipping may comprise packaging the selected one of the plurality of sample nodes in a sample container. As noted above, methods are disclosed further comprising washing the selected one of the plurality of sample nodes prior to said shipping.

The above-mentioned identifying may comprise interrogating a database, while the above-mentioned retrieving may comprise utilizing an optical sensor, automatically or manually operating a sample node removal device, or both. The sample node removal device comprises a laser or a mechanical clipping tool, depending upon the embodiment and overall system requirements, for example.

In some embodiments including performing an analysis of the sample, the analysis is a genomics experiment, whereas in other embodiments, the analysis is a proteomics experiment.

In accordance with yet another aspect of the present invention, a system comprises a sample archive comprising a plurality of sample carriers, each of the plurality of sample carriers configured to support a plurality of discrete sample nodes, a database containing data records associated with ones of the plurality of discrete sample nodes and data records associated with biological analyses, means for receiving a request from a remote client, the request containing information related to performing a selected analysis with selected ones of the plurality of discrete sample nodes, a processor responsive to the means for receiving and operative to retrieve selected ones of the data records from the database, a sample retrieval apparatus responsive to the processor and operative to retrieve the selected ones of the plurality of discrete sample nodes, an assay preparation apparatus responsive to the processor and operative to prepare an assay in accordance with the selected analysis, and means for conducting the selected analysis with the selected ones of the plurality of discrete sample nodes and for providing results of the selected analysis to the processor.

Such a system may further comprise means for packaging the selected ones of the plurality of discrete sample nodes for shipping to the remote client. Embodiments of the system are disclosed wherein the sample retrieval apparatus comprises a sample carrier locator operative to detect a location of selected ones of the one or more sample carriers. As noted above, the sample carrier locator may comprise an optical sensor or a bar code reader. Embodiments of the system include a sample retrieval apparatus comprising a sample node removal device operative to remove the selected ones of the plurality of discrete sample nodes from the plurality of sample carriers.

The sample retrieval apparatus may further comprise an optical sensor; as described above with reference to other aspects of the invention, embodiments of the foregoing system are disclosed wherein the sample node removal device is responsive to signals transmitted from the optical sensor. The sample node removal device comprises a laser in some embodiments, and a mechanical clipping tool in others.

In some systems, the sample node removal device comprises a laser and a mechanical positioning system operative to position the laser relative to the selected ones of the plurality of discrete sample nodes responsive to the signals transmitted from an optical sensor; alternatively, the sample node removal device comprises a mechanical clipping tool and a mechanical positioning system operative to position the mechanical clipping tool relative to the selected ones of the plurality of discrete sample nodes responsive to the signals transmitted from an optical sensor. As noted above, the sample node removal device may comprise a respective transceiver incorporated in each of the plurality of discrete sample nodes. In some embodiments, the analysis performed by the system is a genomics experiment, and in other embodiments, the analysis is a proteomics experiment.

A computer readable medium encoded with data and computer executable instructions is disclosed; the data and instructions causing an apparatus executing the instructions to receive a request from a remote client for performing a selected analysis of a selected sample node maintained on a sample carrier in a sample archive, retrieve data records associated with the selected sample node and the selected analysis from a database, retrieve the selected sample node from the sample carrier, prepare an assay in accordance with the selected analysis, and conduct the selected analysis of a specimen carried on the selected sample node.

The computer readable medium may further cause an apparatus to provide results of the selected analysis and data related to the selected analysis to the remote client. The computer readable medium may further cause an apparatus to transmit control signals to a sample carrier retrieval device operative to retrieve the sample carrier from a sample carrier receptacle at an archive facility. Additionally, this computer readable medium may further cause an apparatus to transmit control signals to a sample carrier storage device operative to place the sample carrier in the sample carrier receptacle. As set forth above with reference to computer readable media aspects, in some embodiments, a computer readable medium may further cause an apparatus to transmit control signals to a sample node removal device operative to locate and to remove the selected sample node from the sample carrier.

In accordance with still another aspect of the present invention, a system comprises a sample archive, a database containing data records associated with samples stored in the archive, means for receiving a request from a remote client, the request containing information related to selected ones of the samples, a processor responsive to the means for receiving and operative to retrieve selected ones of the data records from the database, a sample retrieval apparatus responsive to the processor and operative to retrieve the selected ones of the samples, a sample preparation apparatus responsive to the processor and operative to prepare the selected ones of the samples for analysis, and means for packaging the selected ones of the samples for shipping to the remote client, wherein the sample retrieval apparatus, the sample preparation apparatus, and the means for packaging are operative at a rate sufficient to retrieve, to prepare, and to package in excess of 100 samples per day.

The foregoing system may further comprise means for conducting a selected analysis, such as a genomics experiment or a proteomics experiment, for example, with the selected ones of the samples and for providing results of the selected analysis to the processor.

As noted above, in some embodiments of the system, the sample retrieval apparatus comprises some or all of the following: an optical sensor, a laser, a mechanical clipping tool, or a transceiver.

In some embodiments, the sample retrieval apparatus, the sample preparation apparatus, and the means for packaging are operative at a rate sufficient to retrieve, to prepare, and to package in excess of 200 samples per day; in still other embodiments, the rate may be sufficient to retrieve, to prepare, and to package in excess of 500 samples per day.

The foregoing and other aspects of various embodiments of the present invention will be apparent through examination of the following detailed description thereof in conjunction with the accompanying drawings.

FIG: 6 is a simplified flow diagram illustrating one embodiment of a method of preparing an archive sample for analysis.

Figure 7:
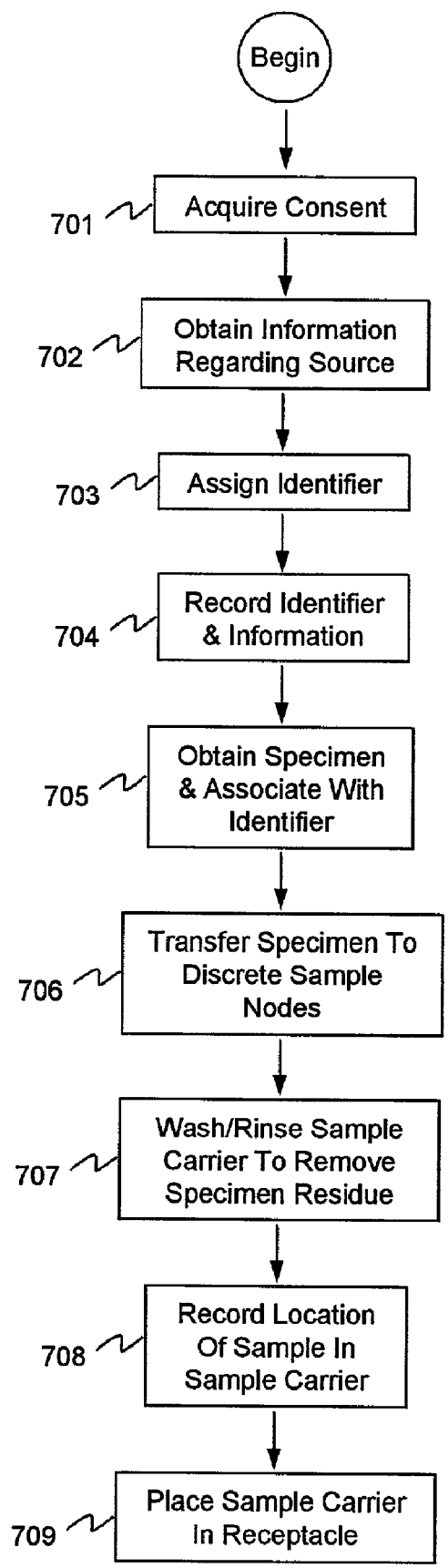

FIG. 7 is a simplified flow diagram illustrating one embodiment of a sample archival method.

Figure 8:
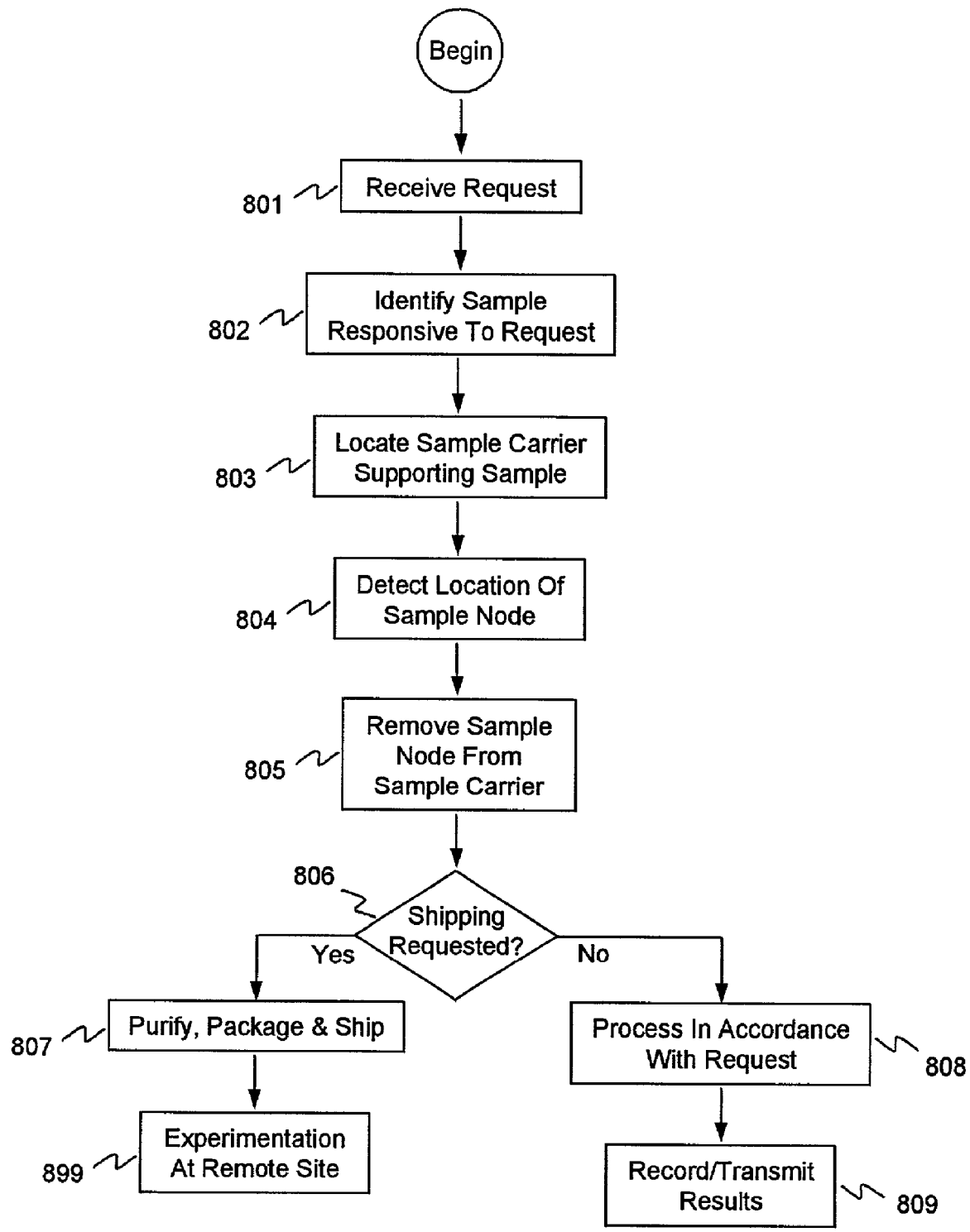

FIG. 8 is a simplified flow diagram illustrating one embodiment of a method of retrieving and preparing an archive sample for analysis.

DETAILED DESCRIPTION

Figure 1:
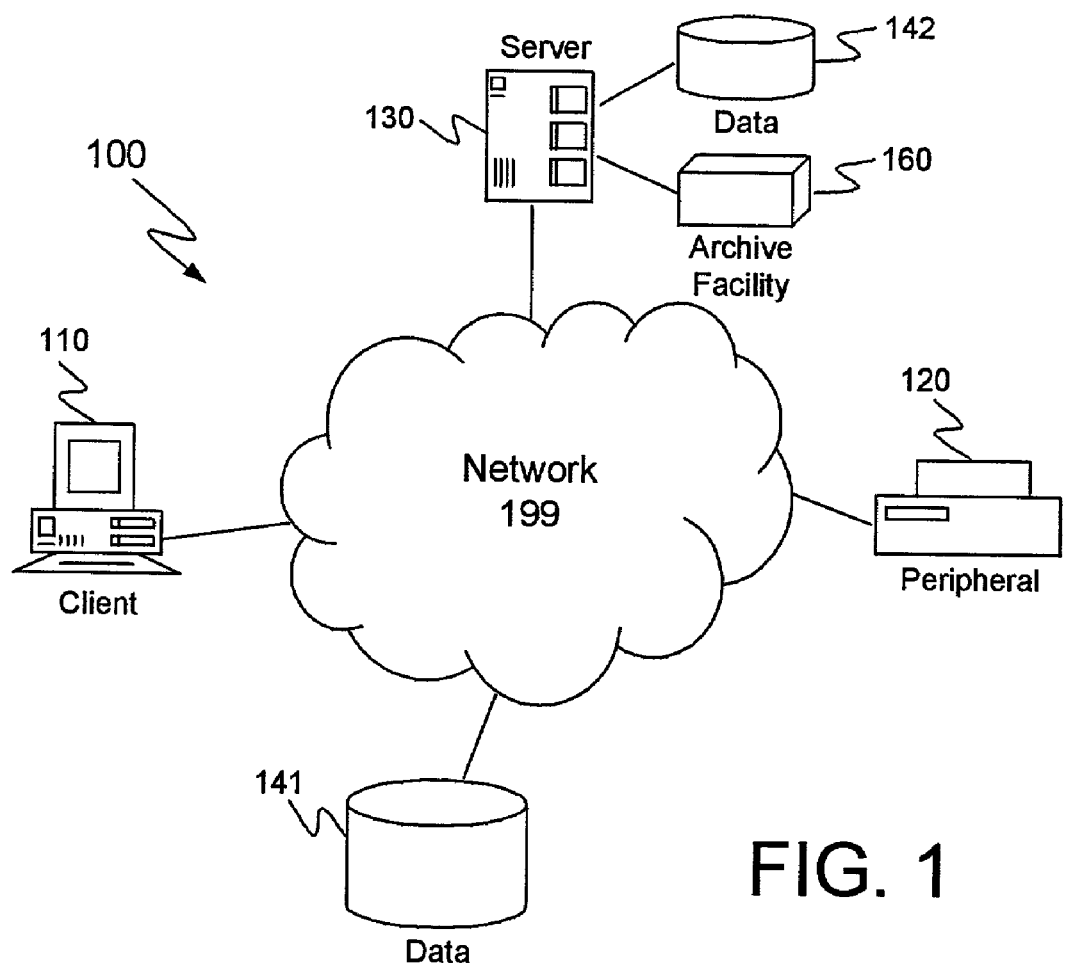
FIG. 1 is a simplified block diagram illustrating one embodiment of an automated sample archival and retrieval system.

Turning now to the drawings, FIG. 1 is a simplified block diagram illustrating one embodiment of an automated sample archival and retrieval system. In the exemplary FIG. 1 embodiment, system 100 generally comprises one or more remote computers or terminals, such as network client 110, coupled to one or more servers, such as server 130, via a communications network 199. System 100 may also comprise data storage media and peripheral equipment, represented by reference numerals 141 and 120, respectively.

For clarity, only one server 130 and one client 110 have been depicted in FIG. 1. Those of skill in the art will appreciate that the arrangement illustrated in FIG. 1 is presented for illustrative purposes only, and that system 100 may be implemented with any number of additional servers, clients, or other components; the number and variety of each device coupled to network 199 may vary in accordance with system requirements. In some embodiments, the functionality of one device, such as peripheral device 120, for example, may reside on or be enabled by another device, such as server 130.

In operation, client 110 may be capable of two-way data communication via communications network 199. In that regard, client 110 may communicate with server 130, peripheral device 120, and data storage medium 141 via network 199 or via one or more additional networks (not shown) which may be coupled to network 199. It will be appreciated by those of skill in the art that client 110, server 130, and other components depicted in FIG. 1 may be coupled via any number of additional networks without inventive faculty.

In some embodiments, client 110 may be a personal computer or workstation, a personal digital assistant (PDA), a wireless telephone, or other network-enabled computing device, electronic apparatus, or computerized system. In operation, client 110 may execute software or other programming instructions encoded on a computer-readable storage medium, and additionally may communicate with server 130, data storage medium 141, and peripheral device 120 for monitor and control applications. For example, client 110 may interrogate server 130 and request transmission of data maintained at data storage medium 142 coupled to, or accessible by, server 130. Additionally or alternatively, client 110 may transmit control signals or requests which may cause device 120 to take some action or to execute a specified function or program routine.

It is well understood in the art that any number or variety of peripheral equipment, such as device 120, may additionally be coupled to network 199 without departing from the essence of the present disclosure. Examples of such peripheral devices include, but are not limited to: servers; computers; workstations; terminals; input/output devices; laboratory equipment; printers; plotters; routers; bridges; cameras or video monitors; sensors; actuators; or any other network-enabled device known in the art. Peripheral device 120 may be coupled to network 199 directly, as illustrated in FIG. 1, or indirectly, for example, through server 130, such that the functionality or operation of device 120 may be influenced or controlled as described below by hardware or software resident on server 130.

As is generally known in the art, server 130 may be embodied or implemented in a single physical machine, for example, or in a plurality of distributed but cooperating physical machines. In operation, server 130 may incorporate all of the functionality of a file server or application server, and may additionally be coupled to data storage medium 142 and sample archive facility 160.

In that regard, information and data records maintained at data storage medium 142 and sample archive facility 160 may be accessible to client 110 through bidirectional data communication with server 130 via network 199.

Network 199 may be any communications network known in the art including, for example: the internet; a local area network (LAN); a wide area network (WAN); a Virtual Private Network (VPN); or any system providing data communication capability between client 110, server 130, storage medium 141, and peripheral device 120. In addition, network 199 may be configured in accordance with any topology known in the art, including star, ring, bus, or any combination thereof.

By way of example, the data connection between components in FIG. 1 may be implemented as a serial or parallel link. Alternatively, the data connection may be any type generally known in the art for communicating or transmitting data across a computer network; examples of such networking connections and protocols include, but are not limited to: Transmission Control Protocol/Internet Protocol (TCP/IP); Ethernet; Fiber Distributed Data Interface (FDDI); ARCNET; token bus or token ring networks; Universal Serial Bus (USB) connections; and Institute of Electrical and Electronics Engineers (IEEE) Standard 1394 (typically referred to as "FireWire") connections.

Other types of data network interfaces and protocols are within the scope and contemplation of the present disclosure. In particular, client 110 may be configured to transmit data to, and receive data from, other networked components using wireless data communication techniques, such as infrared (IR) or radio frequency (RF) signals, for example, or other forms of wireless communication. Accordingly, those of skill in the art will appreciate that network 199 may be implemented as an RF Personal Area Network (PAN).

Storage media 141,142 may be conventional read/write memory such as a magnetic disk drive, a magneto-optical drive, an optical disk drive, a floppy disk drive, a compact-disk read only memory (CD-ROM) drive, a digital versatile disk read only memory (DVD-ROM), a digital versatile disk random access memory (DVD-RAM), transistor-based memory, or other computer-readable memory device for storing and retrieving data.

Sample archive facility 160 may be arranged and configured to maintain a multiplicity of biological or non-biological samples in desiccated form as set forth in more detail below. Additionally or alternatively, archive facility 160 may include mechanical and robotic systems configured and operative to manipulate samples and to facilitate washing, purification, testing, packaging, and shipping thereof. Various testing devices, experimental apparatus, and research equipment may have access to the samples maintained at archive facility 160. Computer hardware and software resident at, or operatively coupled to mechanical and other components at, archive facility 160 may communicate with server 130 as illustrated in FIG. 1. In the exemplary FIG. 1 embodiment, archive facility 160 represents the foregoing samples, equipment, robotics, devices, and computer hardware and software, as well as a network interface enabling bi-directional data communication between computer components in archive facility 160 and server 130.

Figure 2:
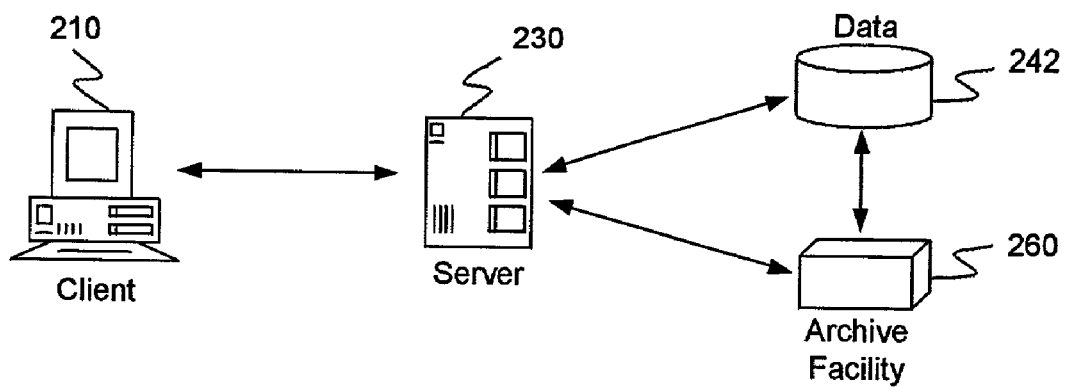
FIG. 2 is a simplified block diagram illustrating the general operation of one embodiment of an automated sample archival and retrieval system.

FIG. 2 is a simplified block diagram illustrating the general operation of one embodiment of an automated sample archival and retrieval system. As illustrated in FIG. 2, client 210 may generally correspond to client 110 depicted and described above with reference to FIG. 1. Similarly, server 230, storage medium 242, and sample archive facility 260 may correspond to server 130, storage medium 142, and archive facility 160, respectively. The components in the FIG. 2 arrangement may incorporate all of the respective functionality set forth above.

Responsive to requests or instructions from client 210, for example, server 230 may be operative to retrieve data or information from storage medium 242 and archive facility 260. Storage medium 242 may comprise a database, for instance, or other data structure configured to maintain data records and other information related to some or all of the following: the number and type of samples maintained in archive facility 260; sample origins or sources; testing or research procedures or protocols; operational parameters of various components incorporated in archive facility 260; and access authorization, passwords, billing information, and the like associated with client 210. The foregoing list is provided by way of example only, and is not intended to be inclusive.

As illustrated in FIG. 2, storage medium 242 and archive facility 260 may be configured to engage in two-way data communication such that computer hardware or systems at archive facility 260 may read data records from, and write data to, storage medium 242. Alternatively, as illustrated and described below with reference to FIG. 3, various data storage media may be incorporated in archive facility 260, for example.

Figure 3:
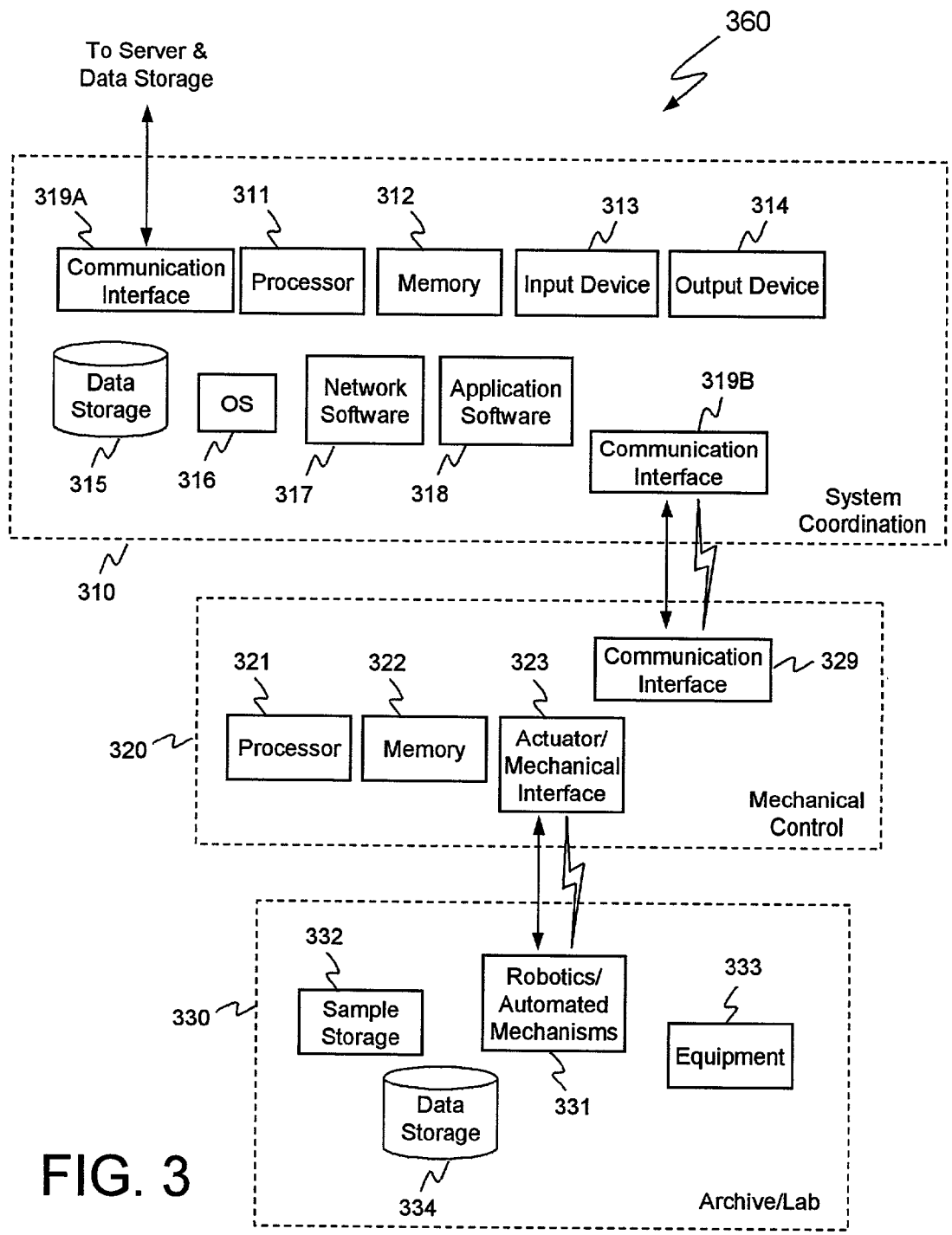
FIG. 3 is a simplified block diagram illustrating components of one embodiment of a sample archive facility and automated archive management system.

FIG. 3 is a simplified block diagram illustrating components of one embodiment of a sample archive facility and automated archive management system. The exemplary FIG. 3 sample archive facility 360 may generally correspond to archive facilities 160 and 260 described above with reference to FIGS. 1 and 2, respectively, and may incorporate all of the functionality and operational characteristics set forth above. Archive facility 360 may generally comprise a system coordination component (coordinator) 310, a mechanical systems control component (controller) 320, and an archive and laboratory component (archive) 330.

System coordinator 310 may include computer hardware and software configured to manipulate or to instruct other system elements as set forth in detail below. Accordingly, coordinator 310 may be embodied in a computer server or other electronic control system, for example, and may be configured to run a multi-tasking operating system (OS 316) as is generally known in the art. Coordinator 310 generally comprises at least one processor 311 coupled to other components described below via a system bus (not shown). Processor 311 may be any microprocessor or microcontroller-based microcomputer known in the art.

The software code or programming instructions for controlling the functionality of processor 311 may be encoded in memory 312 or stored in storage medium 315. Memory 312 and storage medium 315 may be any computer-readable memory known in the art, as discussed above. Additionally or alternatively, some software or instruction code related to operation of processor 311 may reside at a remote device or storage medium 242 as described above with reference to FIG. 2. Network interface hardware and software, such as represented by communication interface 319A and network software 317, respectively, may facilitate the foregoing network communication, and may generally enable any interface known in the art for communicating or transferring files across a computer network as set forth in detail above.

Processor 311 may communicate via the system bus with a plurality of peripheral equipment, including network interface 319A, for example, enabling two-way network data communications as described above. Additional peripheral equipment may be incorporated in or coupled to coordinator 310; in some embodiments, such peripheral equipment may include an input device 313 and an output device 314 enabling a system administrator, researcher, or other technician to interface with coordinator 310 for monitor and control purposes. Examples of peripheral input/output devices may include the following: conventional keyboards, keypads, trackballs, or other input devices; visual displays such as cathode ray tube (CRT) monitors, liquid crystal display (LCD) screens, touch-sensitive screens, or other monitor devices known in the art for displaying graphical images and text; microphones or other audio or acoustic sensor devices; audio speakers; and the like. It will be appreciated by those of skill in the art that peripheral equipment may include suitable digital-to-analog and analog-to-digital conversion circuitry (not shown), as appropriate.

In operation, coordinator 310, under control of processor 311 and OS 316, for example, may execute instruction code or application software 318 configured and operative to provide desired functionality for archive facility 360 as a whole. In some embodiments, for instance, archive facility 360 may be configured to locate and to retrieve selected biological or non-biological samples and to prepare the same for shipping to a remote site for experimentation or further storage. Additionally or alternatively, various components of archive facility 360 may be employed to perform selected experiments with, or related to, retrieved samples. Overall functionality of archive facility 360 may be selectively altered or controlled in accordance with data and computer executable instructions, OS 316, and application software 318 under control of processor 311. In an alternative embodiment, much of the automated functionality of archive facility 360 described below may be manual, or provided by a researcher or technician, for example.

Coordinator 310 may communicate with controller 320 via data signals transmitted through communication interface 319B. In that regard, controller 320 may incorporate a communication interface 329 operative to enable bi-directional data communication with coordinator 310. In one embodiment, the data interface between coordinator 310 and controller 320 may be implemented in the form of a wireline (i.e. "hard-wired"), as represented by the double-headed arrow in FIG. 3. By way of example, the data connection may be a serial, parallel, or Ethernet link, or any other type of communication coupling, such as described above, generally known in the art for communicating or transmitting data across a computer network.

Other types of data interfaces and protocols are contemplated as described above. In particular, as represented by the "lightning bolt" symbol in FIG. 3, coordinator 310 may be configured to transmit data to, and receive data from, controller 320 using wireless IR or RF signals, for example, or other forms of wireless communication. In a wireless embodiment, coordinator 310 and controller 320 may be capable of communicating via the Bluetooth(TM) standard, for example.

Controller 320 may additionally include a processor 321, memory 322, and a mechanical interface 323; though not illustrated in the FIG. 3 embodiment, controller 320 may additionally incorporate or be coupled to a data storage medium, which may store data and configuration instructions related to overall operation of controller 320.

Software code, configuration information, or programming instructions related to or influencing the functionality of processor 321 may be encoded in memory 322, for example; additionally or alternatively, processor 321 may receive data and instructions from coordinator 310 via communication interface 329, or from an additional data source as described above.

In operation, controller 320 may transmit control signals or other data and instructions to affect operation of a device, apparatus, machine, robotic equipment, or other mechanism via mechanical interface 323. The bidirectional data communication interface between controller 320 and the apparatus to be controlled may generally correspond to the data interfaces and protocols described above. As indicated in FIG. 3, controller 320 and the machinery to be monitored or controlled may be coupled via wire-line or wireless communication connections.

It will be appreciated that controller 320 may include one or more additional mechanical interfaces 323, depending upon a variety of factors such as the number of mechanisms to be controlled, the overall capabilities of processor 321, the capacity of memory 322, the data transmission bandwidth of mechanical interface 323, and the desired functionality of the archive facility 360, for example. Additionally or alternatively, archive facility 360 may comprise one or more additional controllers operative to manipulate or to control additional mechanisms; in one embodiment, for example, each machine or device maintained at archive facility 360 may be controlled by a respective dedicated control component such as controller 320.

In the FIG. 3 embodiment, robotic equipment or other mechanisms (robotics 331) to be monitored or controlled by controller 320 are represented as maintained or housed within archive 330. In addition to robotics 331 and associated computer hardware and software required for operation thereof, archive 330 may generally comprise a biological or non-biological sample archive (sample storage 332), instrumentation and equipment 333, and data storage medium 334.

As depicted in the high-level FIG. 3 block diagram, equipment 333 generally represents a wide array of experimental apparatus and instrumentation, laboratory supplies and functional paraphernalia, and the like; the type, construction, and overall configuration of equipment 333 maintained at archive 330 may be a function of the intended operational characteristics of archive facility 360, the state and organization of the samples maintained in sample storage 332, and other factors. Examples of equipment 333 may include test tubes, microtiter or other multi-well plates, laboratory pipettes, storage vessels, shipping boxes and other packaging materials, scales or balances, and so forth. Those of skill in the art will appreciate that the scope of the present disclosure is not limited by the nature or characterization of equipment 333, and that different types of apparatus may be required in accordance with the desired functionality of archive facility 360.

In some embodiments, for example, archive facility 360 may serve as a large scale repository and source for biological or non-biological samples; accordingly, equipment 333 in such an embodiment may include appropriate containers or receptacles for accommodating samples during shipping, packing material and shipping boxes or envelopes, scales or balances for weighing samples or shipping materials, and so forth. Additionally or alternatively, archive facility 360 may be constructed and operative to serve as a central laboratory or experimental services provider. In this latter embodiment, robotics 331 may include proprietary or standardized laboratory modules dedicated to performing specific experiments with biological and non-biological samples, for instance, and equipment 333 may include pipettes and other liquid containers, microtiter plates constructed to receive multiple samples, antigens, reagents and other chemicals, and so forth.

Robotics 331 in the FIG. 3 embodiment of archive facility 360 may represent a wide range of equipment and devices such as, for example: control modules implemented in computer hardware or software; computer-based or electronically controlled machinery, servos, hydraulic systems, and the like; electronic circuits; peripheral equipment such as autoclaves, thermocyclers, or centrifuges; and any other devices to be controlled by controller 320 via mechanical interface 323. In some biological or non-biological sample archives, for example, robotics 331 may be embodied in machine vision apparatus, optical sensors or scanners, bar code readers, and the like, which may identify particular samples from among the plurality of samples in sample storage 332; this identification may be automatic, for example, or under control of an operator or administrator through input/output devices 313,314 at coordinator 310.

Various robotic or automated devices are known in the art for retrieving and transporting samples or sample carriers. Accordingly, robotics 331 may comprise automatically controlled arms or gripping devices which may be translated or otherwise manipulated in three dimensions. Such robotics 331 may generally be configured and operative to retrieve selected samples or sample carriers from sample storage 332 and to manipulate retrieved sample carriers in accordance with data and instructions received from processor 321 at controller 320. Those of skill in the art will appreciate that robotics 331 may comprise computer hardware and software (not shown) sufficient to enable the bidirectional data communication illustrated in FIG. 3; additionally, some embodiments of robotics 331 may include powerful processors, for example, coupled to machine vision or other sample carrier identification devices such as bar code readers or optical sensors as described above.

In addition to placing, identifying, retrieving, and manipulating samples or sample carriers stored or archived at sample storage 332, robotics 331 may further be operative to utilize equipment 333 required for conducting desired operations on or with respect to samples. As noted above, these operations may include washing, purification, alteration, testing or experimental analysis, replacing, packaging, shipping, and the like.

In that regard, robotics 331 may be embodied in, for example: sample storage devices or means operative to place samples or sample carriers into receptacles at sample storage 332; sample location devices, which may employ optical sensors or machine vision technology as described above, for locating particular samples or sample carriers from among the plurality archived at sample storage 332; sample retrieval devices or means for retrieving selected sample carriers from sample storage 332; and sample node removal devices, which also may employ optical sensors as described below. Alternatively, a technician employed at archive facility 360 may place sample carriers into sample carrier receptacles, identify, locate and retrieve sample carriers, and manipulate samples manually.

Data storage medium 334 may be embodied in the types of hardware described above, and may maintain data records related to the samples deposited in sample storage 332, operational parameters of robotics 331 and other mechanized or automated devices, and the availability and variety of equipment 333. For example, storage medium 334 may maintain data records associated with each sample in sample storage 332, including, but not limited to: the nature or type of sample (e.g. blood, DNA, protein, environmental particles or pollutants); the source or origin of the sample; the date the sample was archived; the number of times the sample has been retrieved; the tests or experiments conducted; and the like. Similarly, storage medium 334 may include data records related to the available supply of multi-well plates or other sample vessels at archive 330, the maintenance schedule for various robotic equipment, and so forth. It will be appreciated that data records and other information maintained at storage medium 334 may be transmitted to storage medium 315 at coordinator 310; such transmission may occur periodically, for example, at predetermined time intervals, or responsive to specific requests or interrogations from processor 311.

The nature and variety of robotics 331 and equipment 333 employed at archive 330 may generally be influenced by the manner and form in which samples are maintained and stored in sample storage 332. For example, where samples are stored in conjunction with an identifying bar code label, robotics 331 may comprise a bar code reader. Since, as noted briefly above, certain automated or other robotic systems are known for retrieving, handling, and replacing different types of laboratory containers and sample carriers, sample storage 332 may be constructed and configured for use with existing machines as set forth in more detail below.

Sample storage 332 may generally comprise a plurality of sample carrier receptacles, each of which may be configured to receive one or more sample carriers. Sample carrier receptacles may be implemented as drawers, shelves, or racks, for example. In some embodiments, sample storage 332 may be an environmentally controlled vault or other structure designed to maintain samples at a constant or optimum humidity and temperature; environmental parameters may be selected in accordance with the type and state of the samples. Alternatively, the entire archive 330 may be contained within a single environmentally controlled vault.

Figure 4A:
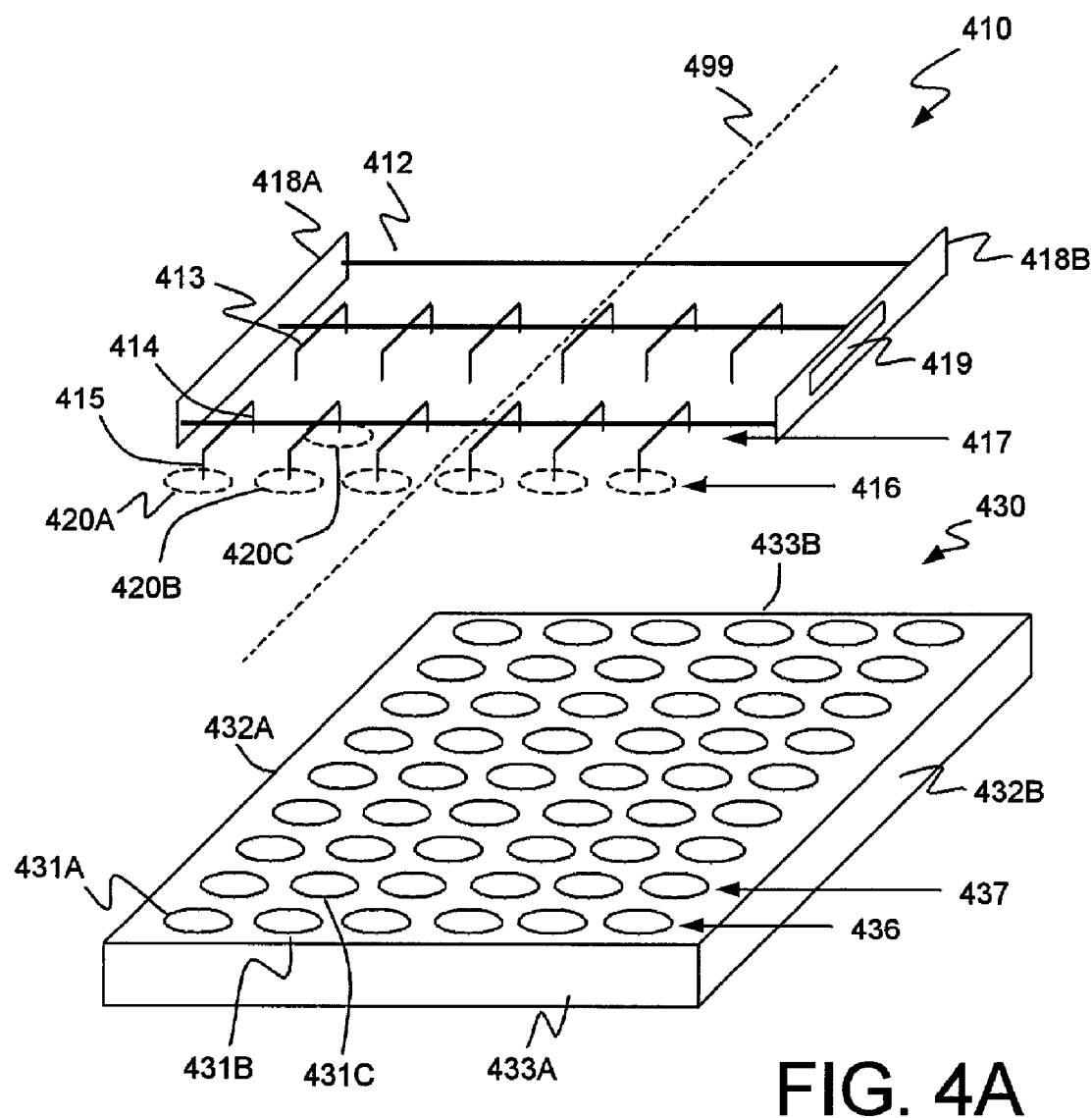
FIG. 4A is a simplified diagram illustrating one embodiment of a sample carrier.

FIG. 4A is a simplified diagram illustrating one embodiment of a sample carrier. In the FIG. 4A embodiment, sample carrier 410 generally comprises a frame structure having a longitudinal axis represented by the dashed line 499. Carrier 410 may include one or more transverse (relative to longitudinal axis 499) members such as designated by reference numeral 412 and a plurality of sample site positioning members 413, each of which may accommodate one or more sample site members 414,415 in a predetermined spatial relationship. Though only three transverse members 412 are illustrated in FIG. 4A, sample carrier 410 may be scaled to include any number of additional transverse members 412 as desired; alternatively, fewer than three transverse members 412 may be appropriate in certain situations.

A structural array, such as designated by reference numerals 420A–420C, configured and operative to maintain a plurality of samples as set forth in more detail below, may be supported at each sample site member 414,415. It is noted that the depiction of structural arrays 420A–420C is representative only, and that certain physical components of structural arrays 420A–420C have been omitted from FIG. 4A for clarity; the particular characterization is not intended to be interpreted in any limiting sense.

As in the illustrated embodiment, sample carrier 410 may be constructed such that each structural array 420A–420C is supported in a predetermined spatial relationship relative to other structural arrays and relative to a respective specimen or sample container. By way of example, structural array 420A may be supported in a position to engage a respective well 431A in a multi-well plate 430, while structural array 420B may be supported to engage a different respective well 431B in multi-well plate 430.

In the exemplary embodiment depicted in FIG. 4A, each structural array in a given row of sample sites on sample carrier 410, e.g. row 416, may be supported in a predetermined spatial relationship relative to a respective specimen or sample container in a corresponding row of wells in multi-well plate 430, i.e. row 436 in this example. Similarly each structural array in row 417 (e.g. structural array 420C) may be supported to engage a respective well in row 437 of multi-well plate 430.

Sample carrier 410 may additionally include longitudinal frame elements 418A,418B which may support transverse members 412. In some embodiments, longitudinal elements 418A,418B may be constructed and operative to support a label, tag, decal, or other identifying indicia 419 which may be unique to sample carrier 410. As is generally known in the art, identifying indicia 419 may incorporate a bar code, a serial number, or other alpha-numeric or symbolic representation, for example, and may distinguish sample carrier 410 from other sample carriers maintained in an archive facility such as illustrated and described above with reference to FIG. 3.

Structural elements of sample carrier 410 may be constructed of any material with sufficient rigidity to support structural arrays 420A–420C in a desired predetermined spatial relationship, which may be influenced, for example, by the configuration or arrangement of respective sample containers such as an array of test tubes or the wells of a multi-well plate. Additionally, longitudinal elements 418A, 418B may be constructed and dimensioned to enable manipulation and transport of sample carrier 410 by robotics or other automated mechanisms; consequently, longitudinal elements 418A,418B may be constructed of appropriate material to withstand forces exerted by handling or gripping mechanisms. Accordingly, the structural elements of sample carrier 410 may be fabricated of polystyrene or various plastics, for example, and may provide suitable stiffness without rendering sample carrier 410 unnecessarily heavy or cumbersome.

Figure 4B:
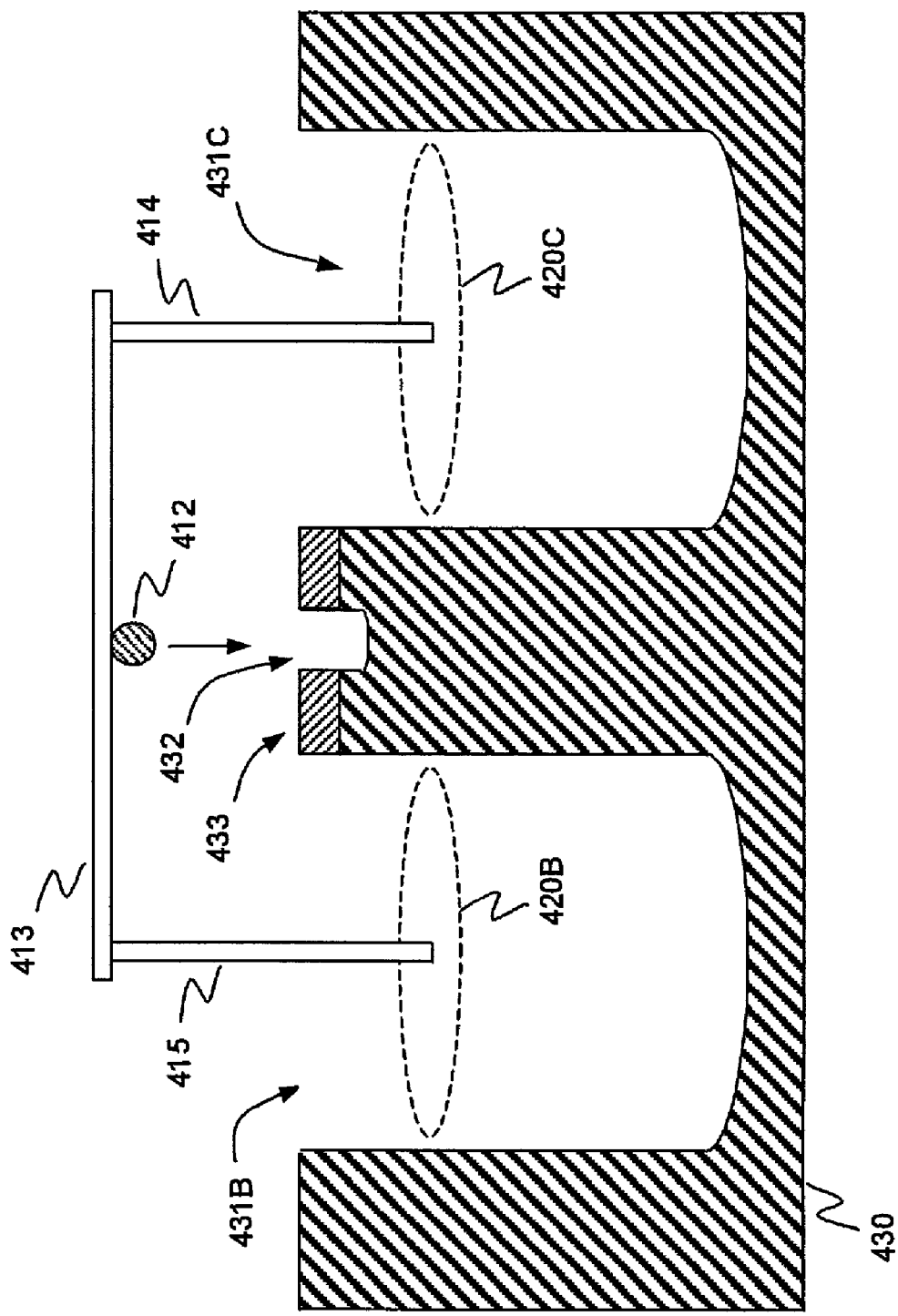
FIG. 4B is a simplified partial longitudinal cross section of a sample carrier constructed to engage a multi-well plate.
Figure 4C:
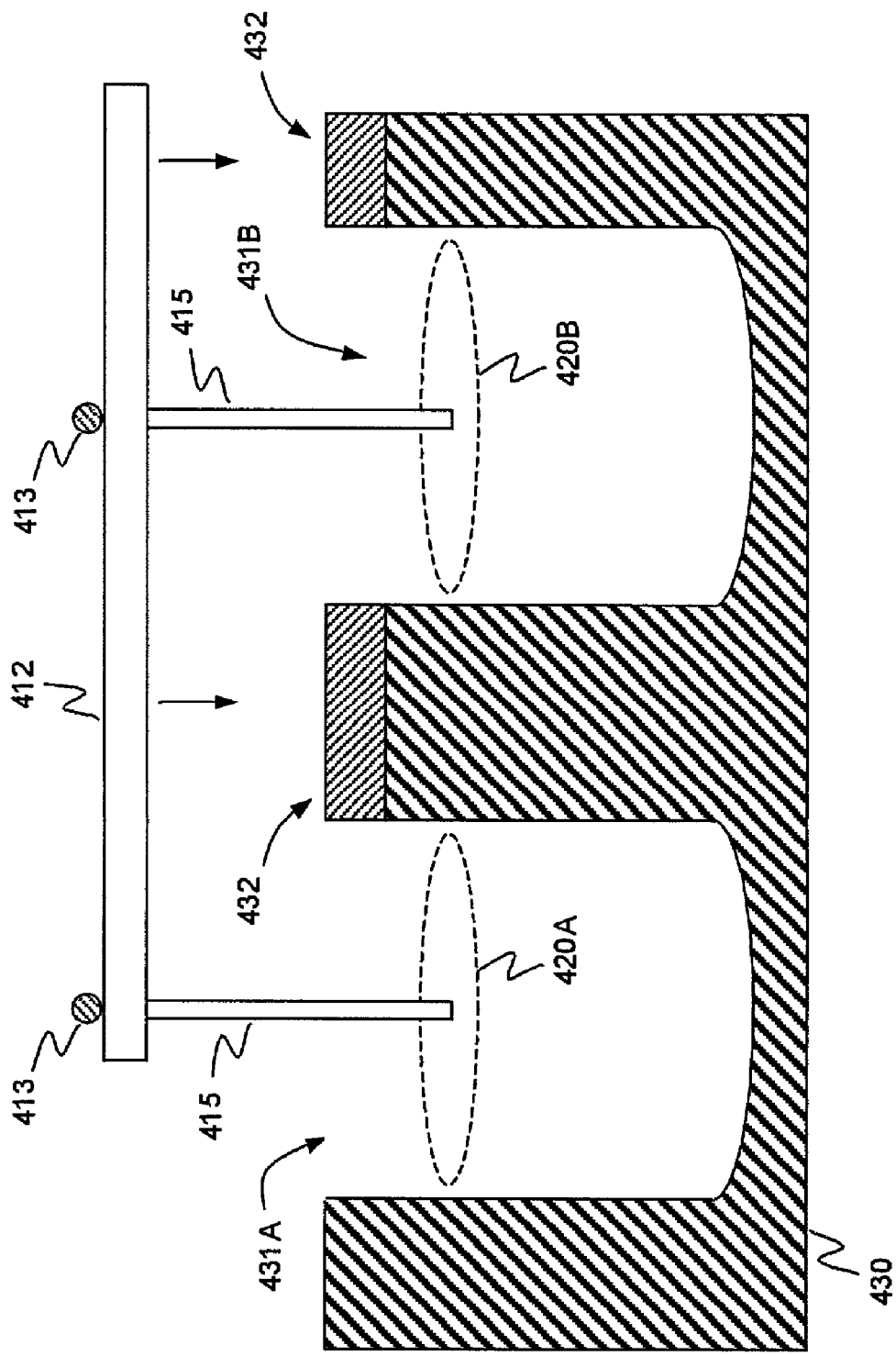
FIG. 4C is a simplified partial transverse cross section of a sample carrier constructed to engage a multi-well plate.

FIG. 4B is a simplified partial longitudinal cross section, and FIG. 4C is a simplified partial transverse cross section, of a sample carrier constructed to engage a multi-well plate. The cross sectional view depicted in FIG. 4B is taken along longitudinal axis 499 in FIG. 4A, whereas the cross sectional view depicted in FIG. 4C is taken along the row 416/436 in FIG. 4A. As indicated in FIGS. 4B and 4C, transverse member 412 may support sample site positioning members 413 such that each sample site member 414,415 (and consequently, its associated structural array 420A–420C) is accurately positioned relative to a respective specimen or sample container (wells 431A–431C) in a multi-well plate 430. As with the illustration in FIG. 4A, structural arrays 420A–420C are depicted in representative form for clarity.

In some embodiments, multi-well plate 430 may include one or more transverse depressions 432; referring back to FIG. 4A, it will be appreciated that depression 432 may be oriented orthogonal to longitudinal axis 499 and disposed intermediate rows 436,437 of wells 431. Depression 432 may be dimensioned to allow acceptance of transverse member 412 when sample carrier 410 is brought sufficiently close to multi-well plate 430. Similarly, multi-well plate 430 may include one or more longitudinal depressions 433 (FIG. 4B) dimensioned to receive sample site positioning members 413 when sample carrier 410 is brought sufficiently close to multi-well plate 430.

Specimen containers such as wells 431A–431C may contain specimen material to be transferred to structural arrays 420A–420C. After appropriate alignment, which may be facilitated by automated mechanisms or robotics, for example, or conducted manually, sample carrier 410 and multi-well plate 430 may be brought into close proximity such that transverse member 412 enters depression 432, sample site positioning member 413 enters depression 433, and structural arrays 420A–420C contact respective specimens contained in wells 431A–431C. In the foregoing manner, specimen material may be transferred to discrete sample nodes (described below with reference to FIGS. 5A–5E) at structural arrays 420A–420C.

Wells such as 431A–431C in various multi-well plates known in the art may be particularly suited to accommodate specimen material in liquid form; it will be appreciated, however, that wells 431A–431C may also carry specimen material in solid or even gaseous form. As noted above, specimens may be biological or non-biological, for example. Biological specimen material may include biopolymers such as proteins or other polynucleotides, e.g. DNA. Examples of non-biological specimens may include chlorofluorocarbons or other environmental or atmospheric pollutants.

Following transfer of sample material to structural arrays 420A–420C, sample carrier 410 may be engaged with a clean, or previously unused, multi-well plate 430 for sample storage and preservation. In this embodiment, sample containers such as wells 431A–431C of multi-well plate 430 may not contain any specimens or other material, and may protect samples maintained at structural arrays 420A–420C from contamination introduced by external sources or by contact with other items. Since depression 432 is configured to accommodate transverse member 412 and depression 433 is configured to accommodate sample site positioning member 413, the combination of sample carrier 410 and multi-well plate 430 may accept a cover (not shown) as is generally known in the art of preserving samples in multi-well plates.

Longitudinal elements 418A,418B may extend beyond the longitudinal sides 432A,432B of multi-well plate 430 and the sides of any cover or lid. A gripping or handling apparatus oriented for use along longitudinal axis 499 may engage longitudinal elements 418A,418B and remove sample carrier 410 (and any lid disposed thereon) from multi-well plate 430; on the other hand, a gripping or handling apparatus oriented for use along the transverse axis may engage transverse sides 433A,433B of multi-well plate 430, and consequently, the entire assembly of multi-well plate 430, sample carrier 410, and cover. In the foregoing embodiment, a standard plate cover may be modified to allow protrusion of transverse members 412 and longitudinal elements 418A,418B.

Figure 5A:
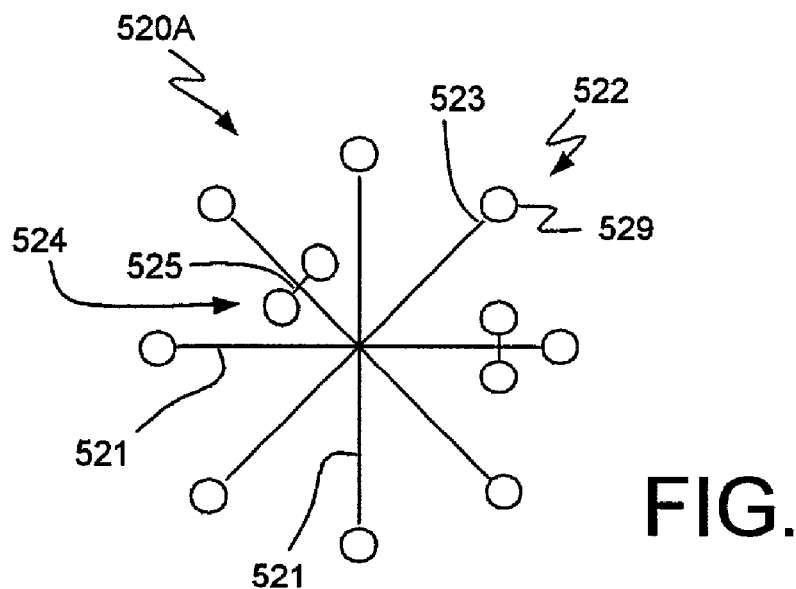
FIG. 5A is a simplified diagrammatic plan view illustrating one embodiment of a structural array employed by a sample carrier.

FIG. 5A is a simplified diagrammatic plan view illustrating one embodiment of a structural array employed by a sample carrier. Structural array 520A generally corresponds to those represented and described above with reference to FIGS. 4A–4C. The arrangement and overall configuration of structural array 520A is provided by way of example only. In some embodiments, structural array 520A may be fabricated of the same material, such as polystyrene or other polymer, for example, as the sample carrier to which it is attached.

Structural array 520A generally comprises a plurality of sample structures such as designated by reference numerals 522 and 524. Sample structures 522,524 may be maintained in a predetermined spatial relationship by radial elements 521 or other suitable structural components. In the exemplary embodiment, a sample node (represented by the small circles in FIG. 5A, one of which is designated by reference numeral 529) may be removably attached to structural array 520A at a respective one of the sample structures 522,524; i.e. each sample structure 522,524 may be operative to support a discrete sample node 529. In turn, each sample node 529 may be operative to carry a discrete sample, such as biological or non-biological sample material, for example. Such samples may include, for example, proteins or polynucleotides.

Sample nodes 529 may be removably attached to sample structures 522,524 at attachment points 523,525, respectively. In some embodiments, attachment points 523,525 may be free from specimen material or other contaminants such that selective removal of sample nodes 529, even by mechanical means requiring physical contact with attachment points 523,525, does not introduce cross contamination risks generated by foreign material, residue from previous removal operations, or other particulate matter.

Figure 5B:
FIG. 5B is a simplified illustration of various embodiments of a sample node.

It will be appreciated that sample nodes 529 need not be circular, nor of uniform size, as represented in FIG. 5A, but may be formed in any of numerous other shapes and sizes. FIG. 5B is a simplified illustration of various embodiments of a sample node. Those of skill in the art will appreciate that several polygons, polyhedrons, and spherical or oblong shapes are contemplated and may be selected based upon various factors such as the desired node size and density, the saturation limit of the material used for nodes 529, the accuracy and precision of the device used to remove nodes 529 as described below, and the like. The present disclosure is not intended to be limited by the shape, size, or dimensional characteristics of sample nodes 529.

A sample node 529 such as illustrated and described may generally comprise, or be constructed entirely of, a sample support medium; in some embodiments, for example, sample node 529 may simply be coated with a selected sample support medium. In accordance with one aspect of the present invention, sample support media for use at sample nodes 529 may be embodied in paper or cellulose, polystyrene, plastic, or other suitable support material constructed and operative to serve as a long-term storage mechanism for biological or other samples in a desiccated form. Specimen material in solid, liquid, or gaseous form may be brought into contact with the sample support medium and stored as samples at discrete sample nodes 529.

In some embodiments, for example, such a sample support medium may maintain desiccated samples of biopolymers, including DNA and proteins, or non-biological samples, including fluorocarbons or chlorofluorocarbons (CFCs) and synthetic chemical compounds. As noted above, filter paper substrate embodiments are currently known in the art; the present disclosure is not to be construed as so limited, however. A support medium suitable for implementation at sample nodes 529 may generally comprise any appropriate material known in the art or developed and operative in accordance with known principles, and may be selected in accordance with binding properties as a function of the type of sample to be carried and maintained.

In that regard, an appropriate sample support medium may be solid or porous, for example, depending, in part, upon the type of specimen to be stored as samples at discrete sample nodes 529. Additionally or alternatively, sample support medium may be treated with one or more chemical compounds or derivatized, for instance, to manipulate various binding properties prior to contact with a specimen. Positive or negative electrical charges, chemical compositions, binding characteristics, antibodies, lectins, porosity, and other operational factors for sample nodes 529 may be selected in accordance with the type of sample support medium implemented and the type or nature of any processes performed thereon.

Biological and non-biological samples may be stored in a controlled environment. In that regard, humidity, temperature, and other environmental factors may be controlled in a fireproof vault or other structure employed as an archive as set forth above. In some embodiments, environmental conditions may be selectively altered depending, for instance, upon the nature of the samples, the composition of the sample support medium employed at sample nodes 529, or both, to preserve longevity of the samples for decades. In a DNA archival embodiment, for example, the sample support medium may include a chemically treated surface or structure, serving to lyse particular specimen cells and to immobilize the DNA structure to the sample support medium or substrate at discrete sample nodes 529. Additionally or alternatively, preservatives may be applied, embedded, impregnated, or otherwise incorporated onto or into the sample support medium; such preservatives may ensure the stability and fidelity of the DNA structure for tens of years. Sample nodes 529, which may be characterized by discrete pellets or spheres as represented in FIGS. 5A and 5B, may be automatically removed from a sample carrier and selectively deposited in particular wells disposed in multi-well plates; samples deposited in particular wells may, in turn, be selected for subsequent processing (e.g. such as with polymerase chain reaction (PCR) assays, and the like).

Cross contamination is virtually eliminated by storing the samples on discrete sample nodes 529. In some instances, sample nodes 529 may be optically separated from the sample carrier, thereby avoiding any mechanical contact involving a mechanical sample removal device during retrieval, extraction, purification, packaging, and shipping. Moreover, since a sample carrier such as illustrated in FIGS. 4A–4C may be amenable to manipulation by standard robotics, an entire archive facility may be easily automated to achieve high I/O rates (for example, greater than one hundred samples per day).

DNA which is archived and retrieved as set forth above with reference to FIGS. 3–5B may be well suited for large-scale genetic analysis, and may yield samples which are superior (relative to conventional liquid phase or cryogenic technologies) for pharmacogenetics or other types of genetic discovery analysis. Specifically, implementation of discrete sample nodes 529 may automatically standardize the quantity and quality of DNA storage due to the inherent loading properties of the sample support medium and any embedded chemicals serving to diminish PCR inhibitors; accordingly, the requirements and complexities of quantification procedures following purification in conventional DNA extraction may be simplified, reduced, or eliminated entirely. Additionally, desiccated archive samples are not continuously degraded during repeated freezing and thawing cycles as is common in cryogenic systems.

Figure 5C:
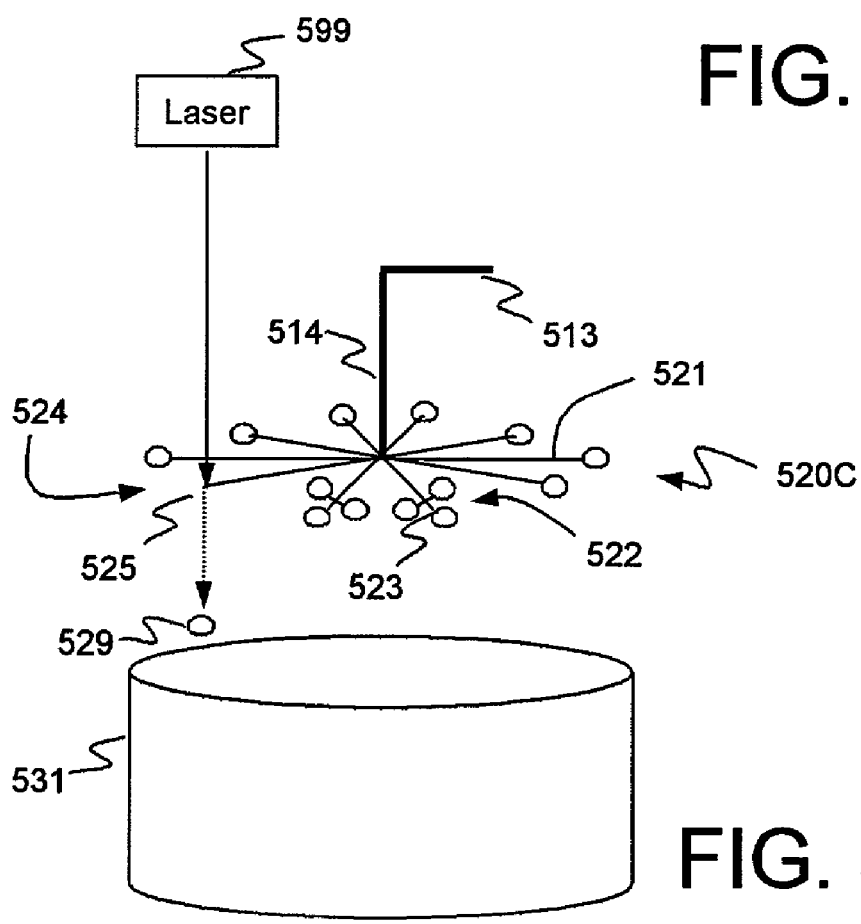
FIG. 5C is a simplified block diagram illustrating one embodiment of a system and method of removing a sample node from a sample carrier structural array.

FIG. 5C is a simplified block diagram illustrating one embodiment of a system and method of removing a sample node from a sample carrier structural array. As indicated, a removed sample node 529 may be deposited in a sample container such as a well 531 in a standard or modified multi-well plate (FIGS. 4A–4C); the remainder of the sample carrier to which structural array 520C is attached and the remainder of the multi-well plate have been omitted from FIG. 5C for clarity.

Structural array 520C may be supported from a sample carrier by a sample site positioning member 513 and a sample site member 514. As set forth in detail above, a discrete sample node 529 may be attached to sample structure 524 at attachment point 525. In the FIG. 5C embodiment, a laser 599 may provide sufficient energy in the form of coherent light to attachment point 525 to remove sample node 529. Those of skill in the art will appreciate that other means, mechanisms, or devices may be employed to remove sample node 529 from structural array 520C; accordingly, a cutting or clipping apparatus, micro-electromechanical devices (MEMS), or electrical circuit elements such as fuses, for example, may be employed in lieu of laser 599 to provide energy necessary to separate sample node 529 from sample structure 524.

As discrete sample nodes 529 are removed from structural array 520C during the useful life of a given sample carrier, fewer sample structures 522,524 may be supporting a sample node 529, i.e. fewer sample nodes 529 remain. Accordingly, the laser in the exemplary FIG. 5C embodiment may be enabled to identify or otherwise to ascertain the location of a particular sample node 529 targeted for removal. In that regard, each sample structure 522,524 and its respective attachment point 523,525 may be addressed and catalogued, for example.

Addressing or location information may be stored in a data storage medium as described above with reference to FIG. 3, and may enable laser 599 or other sample node removal means to identify and to target a specific attachment point 523,525 supporting a discrete sample node 529 on structural array 520C. Where the particular structural arrangement or configuration of structural array 520C is known and sample node addressing information is stored as one or more data records, computerized robotic systems or computer-targeted laser 599 may be controlled precisely to remove a selected sample node 529; similarly, the system may be apprised, through updated data records, of sample nodes which have been removed such that a detailed search of the entire structural array 520C may not be required for subsequent sample node removal operations.

Additionally or alternatively, laser 599 or another sample removal device, such as a robotic clipping mechanism, for example, may be equipped with machine vision or other optical sensors. In this embodiment, a sample locator device may gather optical information which may subsequently be used to guide a sample node removal apparatus such as laser 599 in an interactive manner, ie. the system may methodically examine each sample structure 522,524 in a predetermined order, for example, or under control of an operator, until a sample structure 522,524 supporting a sample node 529 is detected. This embodiment may be implemented in situations where the configuration or orientation of all the components of structural array 520C is not known or has changed (e.g. due to breakage or structural failure), or where the history of sample node removal operations for a given structural array 520C is not known; in such situations, a detailed "map" or other indication of remaining sample node locations may not be available.

Figure 5D:
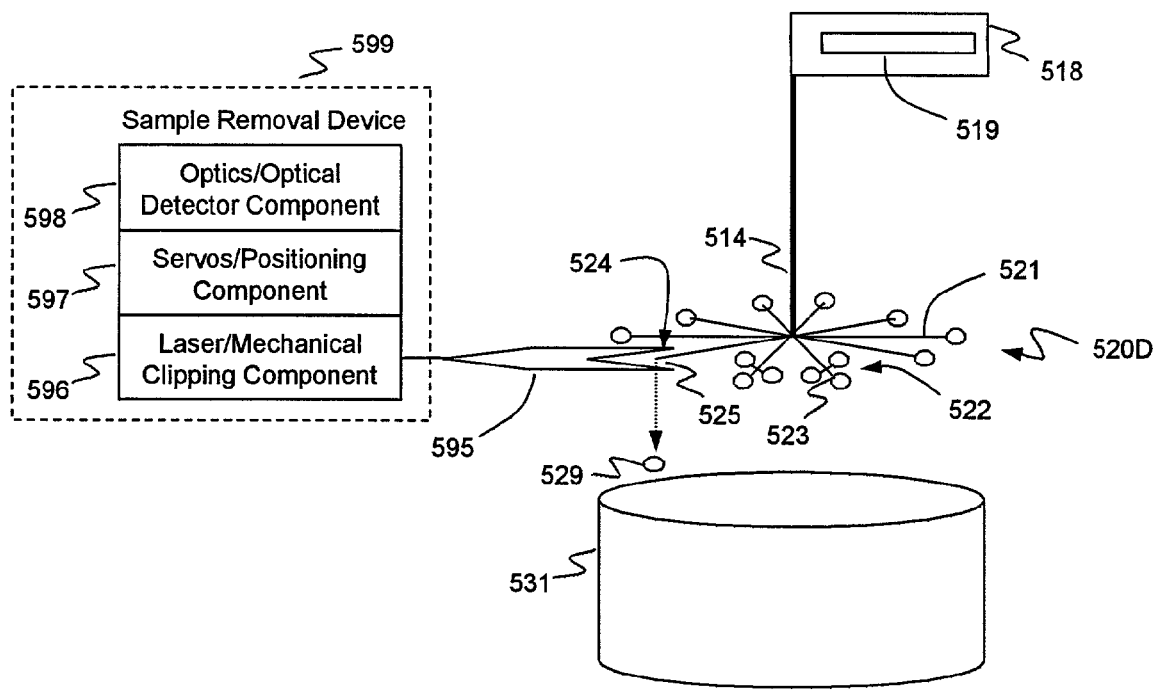
FIG. 5D is a simplified block diagram illustrating another embodiment of a system and method of removing a sample node from a sample carrier structural array.

FIG. 5D is a simplified block diagram illustrating another embodiment of a system and method of removing a sample node from a sample carrier structural array. As in the FIG. 5C embodiment, a removed sample node 529 may be deposited in a sample container 531 such as a well in a standard or modified multi-well plate, a test tube, or other vessel. The omission of a sample structure positioning member from FIG. 5D is representative of the fact that a given sample carrier may support only a single structural array 520D.

In this embodiment, structural array 520D may be supported simply by a sample site member 514, which may include an identification structure 518 bearing a label or other identifying indicia 519 such as a bar code, serial number, and the like, substantially as described above.

A sample removal device 599 may be employed to remove sample node 529 from structural array 520D; accordingly, sample removal device 599 may generally comprise an optical component 598, a positioning component 597, and a clipping component 596.

Optical component 598 may generally comprise machine vision technology, video cameras, or other optical sensors which are capable of identifying or locating the elements of structural array 520D using instruments or receptors which are sensitive to various portions of the electromagnetic spectrum. In this embodiment, optical information (from the visible portion of the spectrum) or other electromagnetic information (such as microwave or infrared frequencies, for example) may be used to ascertain the configuration and arrangement of structural array 520D. The foregoing information may be used to automate the remaining components of sample removal device 599, for example; a completely automated robotic system may be developed around the functionality of optical component 598. Alternatively, output from optical component 598 may be transmitted or otherwise displayed in visual form for a system operator, who may control other elements of sample removal device 599 in accordance with optical information regarding structural array 520D obtained and provided by optical component 598.

Whether automated or operator-controlled, positioning component 597 may be employed to guide clipping component 596 to an appropriate position relative to structural array 520D to remove a targeted sample node 529. In that regard, positioning component 597 may include some or all of the following: servos; motors; hydraulic or electromechanical arms, appendages, or conveyors; gyroscopes; rotating shafts; pistons; gears; guide rails; support beams; and other elements generally known in the art for translating and articulating apparatus in three dimensions.

As set forth above, positioning component 597 may be operative to move clipping component 596 or another sample node removal apparatus. Additionally or alternatively, positioning component 597 may be constructed and operative to move structural array 520D or the sample carrier to which it is attached. For example, structural array 520D or the sample carrier may be mounted on a movable stage which translates in one or two dimensions. Whether positioning component 597 moves clipping component 596, structural array 520D, or both, it will be appreciated that such a mechanical positioning system may bring a sample node removal device into a desired position relative to structural array 520D, i.e. enabling removal of a targeted sample node 529.

As noted above with reference to FIG. 5C, various devices such as lasers, micro-electromechanical devices (MEMS), or electrical circuit elements may be employed to remove a targeted sample node 529 from a structural array. The exemplary FIG. 5D embodiment of clipping component 596 comprises a mechanical clipper 595 which may be operative to sever sample structure 524 at attachment point 525. It will be appreciated that use of a mechanical device such as clipper 595 may require physical contact with sample structure 524 during normal operation; to avoid risk of cross contamination from one sample removal operation to the next, it may be desirable to ensure that sample structure 524 is free of specimen material or other possible contaminants at the point at which clipper 595 makes contact.

Figure 5E:
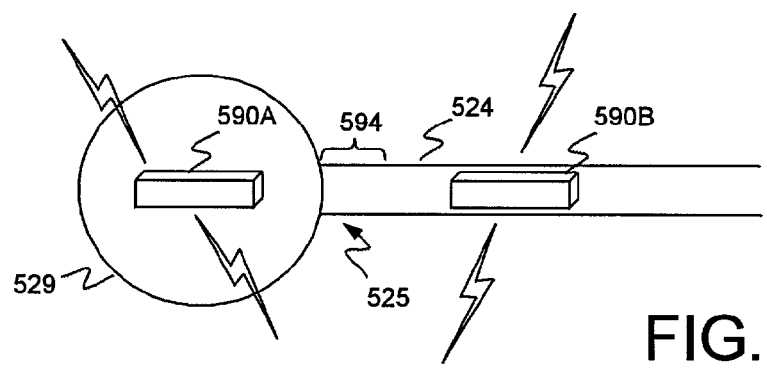
FIG. 5E is a simplified block diagram illustrating one embodiment of a sample node identification or location system.

FIG. 5E is a simplified block diagram illustrating one embodiment of a sample node identification or location system. To maximize the density of samples maintained in an archive facility such as illustrated in FIGS. 1–3, biomolecules (such as DNA and proteins, for example) or non-biological samples to be archived may be tagged electronically for subsequent identification. Recently, micro-transceiver systems have been developed by researchers and proposed for use in active drug delivery techniques. As illustrated in FIG. 5E, for example, an electronic microtransceiver 590A, may be integrated into a discrete sample node 529; additionally or alternatively, a transceiver 590B may be attached to, or integrated into, sample structure 524 proximal to attachment point 525.

As set forth above, biomolecules or other sample material may be attached on the surface (or may penetrate into the sample support medium) of sample node 529 for high density archiving. A micro-transceiver 590A,590B may transmit omni-directional RF signals, for example, enabling a receiver at a robotic system to identify and to locate sample node 529 using associated signature signal frequencies, transmission patterns, or other information. In this embodiment, a unique signal transmitted by transceiver 590A,590B may be received by the positioning component 597 in FIG. 5D and used to direct the positioning of robotic instrumentation or sample removal component 596.

Additionally or alternatively, a remote control system maintained at an archive facility may transmit signals to transceivers 590A and 590B to initiate operation of MEMS, for example, or to activate microcircuits or circuit elements operative to remove sample node 529 from sample structure 524. In the foregoing manner, sample node removal may be triggered electronically based upon signals transmitted to transceivers 590A and 590B.

As described above, it may be desirable to ensure that sample structure 524 is free of specimen material or other possible contaminants to avoid risk of cross contamination. The FIG. 5E embodiment illustrates a region 594 representing the point at which a mechanical clipping device may make contact with sample structure 524. As set forth in more detail below, after specimen material is transferred to sample node 529, sample structure 524 or the entire structural array or sample carrier, for instance, may be washed or cleaned to remove contaminants or specimen residue from region 594 or the entirety of sample structure 524.

Figure 6:
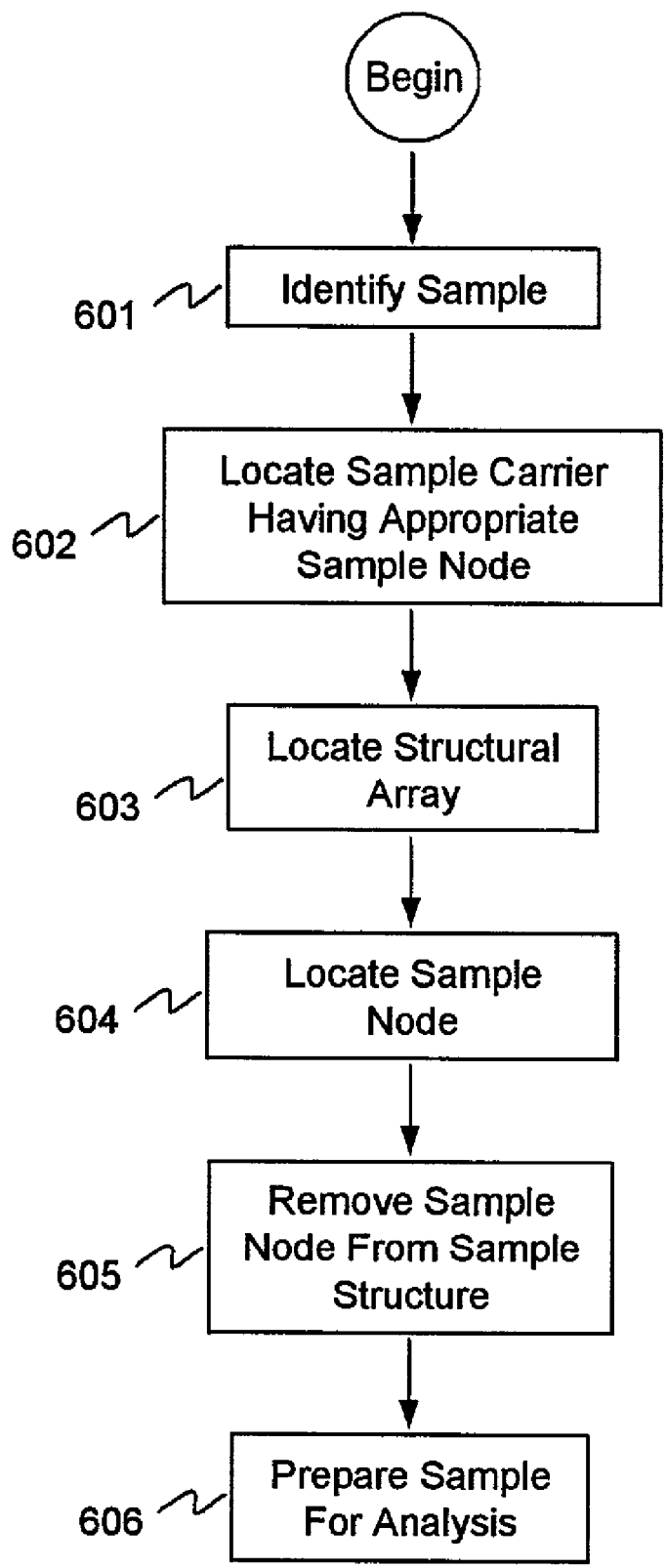

FIG. 6 is a simplified flow diagram illustrating one embodiment of a method of preparing an archive sample for analysis. An archive sample to be analyzed may be identified or selected at block 601. For example, a researcher may browse a list or catalogue of available samples (e.g maintained at an archive facility as described above with reference to FIGS. 1–3); the list of archive samples may additionally be cross-referenced with data records containing information related to sample sources as set forth in detail above, for example. In this sense, identifying or selecting the sample to be analyzed may simply represent a process of designating or otherwise indicating a sample or type of sample which may be appropriate for the intended analytical procedure.

Upon identification of a suitable sample or sample type, a sample carrier which supports one or more appropriate sample nodes (i.e. a sample node carrying the selected sample) may be identified and located as indicated at block 602. As with identification of a sample at block 601, locating a sample carrier at block 602 may be executed manually, for example, by a researcher or a technician; alternatively, identification of a sample and location of a sample carrier may be automated, for example with bar code readers and robotic sample carrier retrieval apparatus, as described above with reference to FIGS. 3 and 5.

At blocks 603 and 604, a structural array and a sample node may be identified and located as set forth above with reference to FIGS. 5C–5E. Accurate address or location information may be maintained in a data storage medium such that location of a structural array and a particular sample node may be accomplished without the use of optical systems or machine vision techniques. In some embodiments, however, it may be desirable to identify and to locate a discrete sample node actively, for example, with the assistance of optical sensors or video signal information.

Removal of one or more identified sample nodes at block 605 may require implementation of a sample node removal device or means for separating the sample node from its respective sample structure. As set forth above, suitable devices or apparatus include, but are not limited to, the following: targeted lasers; automated or manually controlled clipping, cutting, slicing, or breaking tools; programmable MEMS, which may be small enough and sufficiently agile to maneuver on the components of the structural array illustrated in FIGS. 5A–5E; electrical fuses which, when blown, may create sufficient heat to destroy the attachment point thereby to separate a sample node from its respective sample structure; or any other mechanisms configured and operative to deliver enough energy to the sample structure to remove the sample node.

As described above, each structural array, and consequently its sample nodes, may be positioned and dimensioned in a predetermined spatial relationship, particularly with respect to one or more sample containers. A sample node removed from a structural array (block 605), may be deposited in a sample container such as a well in a multi-well plate, a test tube or other experimental or storage vessel, a paper or cardboard bindle, a shipping container, and the like.

As indicated at block 606, a removed sample node may be prepared for analysis. The preparation indicated in the FIG. 6 embodiment may represent any or all of the following, inter alia: addition of reagents or other chemicals to a sample container; purification of the sample removed from the sample carrier; washing, packaging, and shipping or other transportation to a remote site for analysis; and so forth.

FIG. 7 is a simplified flow diagram illustrating one embodiment of a sample archival method. As indicated at block 701, the storage or archival process may generally begin with acquiring consent from a patient or other specimen source. Much like the conventional archiving process, informed consent may be obtained by a professional recruiter after explaining the nature of the research to be conducted at an archive facility and any techniques or technologies employed by the archive facility to ensure specimen source confidentiality. It will be appreciated that, in the case of non-biological specimens, for example, acquiring informed consent at block 701 may be neither possible nor necessary.

Information concerning or relating to the specimen source may be obtained as indicated at block 702. By way of example, a questionnaire or other form may be completed by the specimen source (e.g. a patient or a patient's guardian or representative) with the aid of a trained professional; the questionnaire or form may be electronic, prompting computer input responses. Additionally or alternatively, some or all of the information obtained from the specimen source may be oral or hand written; in this exemplary embodiment, a technician or data entry professional may input relevant information into a computer for recordation in a database. A standardized or modified computer spreadsheet or other proprietary application software which is compatible with the database may be used for data recordation. In some embodiments, data transcription errors may be minimized and maximum efficiency may be achieved where source- and specimen-specific information is input directly into a computerized system.

As depicted at block 703, a unique code, serial number, or other identifier may be assigned to the information associated with the specimen and its source. As illustrated and described in detail above with reference to the sample carriers of FIGS. 4A and 5D, a respective bar code or other identifying indicia may be used to identify specific samples. In the case of specimens and source-specific information, such an identifier may be assigned early in the archival process, possibly even before the specimen is obtained, as in the FIG. 7 embodiment. Identification of a specimen source and accurate association and cross-referencing with, for instance, the medical history of the source or other relevant information, may facilitate efficiency and proper interpretation of results in large-scale DNA or genomic studies, for example.

Data specific to the specimen and the source may be recorded as data records in a database as indicated at block 704. As is generally known in the art, data records may be accessed or retrieved in accordance with the unique identifier associated therewith and assigned as set forth above. As illustrated and described in detail above with reference to FIG. 3, data storage media serving as central information repositories may be maintained at various locations in an archive facility. Data may be transmitted to an archive facility, for example, via a network connection such as described above; in that regard, a secure internet connection employing Secure Sockets Layer (SSL) encryption technology (128-bit encryption) or a VPN connection (168 bit encryption) may ensure data integrity and confidentiality of sensitive information. Information associated with each contributing specimen source and transmitted to the archive facility may be formatted in accordance with database requirements, for example, and subsequently made available to archive facility clients via the network connection; in some embodiments, database formats and access authorizations may be selected to preserve specimen source confidentiality.

A specimen may be obtained from the source and associated with the correct unique identifier as indicated at block 705. For example, blood may be drawn from a patient by a member of a pathology nursing staff. A portion of a standard blood draw (e.g. approximately 1–5 ml of a total 10 ml draw) may be used to create samples for use in conjunction with a sample carrier as described in detail above with reference to FIGS. 4 and 5.

In accordance with this embodiment, a sample carrier may generally support one or more structural arrays, each comprising a plurality of discrete sample nodes. As set forth above, each sample node may be operative to carry a sample on a sample support medium. Some of the blood drawn may be deposited in a specimen container, for example, a test tube or one or more wells in a multi-well plate. The structural arrays of the sample carrier may selectively be placed in proximity to the respective specimen containers such that the plurality of sample nodes are selectively exposed to respective specimens. The sample support medium at the sample nodes may absorb, lyse, or otherwise bind the blood spotted in the respective specimen containers. In the foregoing exemplary manner, specimen material may be transferred to discrete sample nodes as represented at block 706. In some embodiments, preservatives may be applied or the sample nodes may be allowed to dry such that each sample is maintained in desiccated form.

Sample nodes or entire sample carriers may be washed or rinsed, for example with detergents or other chemicals, to remove specimen residue or other contaminants from sample structures as described above. The cleaning process, represented at block 707, may reduce the risk of cross contamination potentially introduced by operation of the sample removal device.

As noted above with reference to FIGS. 4A and 5D, sample carriers may be bar-coded, labeled, tagged, or otherwise provided with unique identifying indicia, decipherable by an optical scanner or machine vision technology, which may facilitate automated or manual sample and sample carrier tracking. A bar code or other identification on a particular sample carrier may provide information related to the source of the specimen used for each structural array on the sample carrier; further, the identifying indicia may also provide information related to the structural arrangement or configuration of each structural array, i.e. the number of discrete sample nodes in a particular structural array, information concerning the spatial orientation of each discrete sample node, and so forth. The location of each sample within the sample carrier may be recorded as indicated at block 708; this recordation may be coordinated with production of the bar code or other indicia for the sample carrier.

Covered storage carriers may be shipped to an archive facility from remote locations, i.e. wherever specimens are obtained, typically by express mail. Since shipping blood or other biological samples in a desiccated or dry state does not require treatment as a hazardous material, sample carriers supporting desiccated samples may be conveniently shipped anywhere in the world.

At an archive facility such as described above with reference to FIG. 3, robotics or automated mechanical systems may be used to place sample carriers in receptacles (block 709). Receptacles may be embodied in shelves, drawers, racks, or other structures constructed to receive sample carriers; accordingly, the form and particular structural configuration of receptacles at an archive facility may generally be a function of the type and configuration of the sample carriers to be stored.

In one embodiment, an automated shelf or receptacle for storage and retrieval may be constructed to accommodate a sample carrier engaged with a multi-well plate as described above with reference to FIG. 4A. In this embodiment, longitudinal frame elements of the sample carrier may extend beyond the multi-well plate. A robotic gripping mechanism may grasp the entire assembly (i.e. the sample carrier and the multi-well plate), or only the sample carrier, depending upon the orientation of the gripping mechanism relative to the receptacle.

It will be appreciated that various alternatives exist with respect to the FIG. 7 embodiment, and that the presented order of the individual blocks is not intended to imply a specific sequence of operations to the exclusion of other possibilities; the particular application and overall system requirements may dictate the most efficient or desirable sequence of the operations set forth in FIG. 7. For example, specimen acquisition and association with an identifier (represented at block 705) may precede block 704, or may even occur prior to obtaining source-specific information at block 702, provided that appropriate provisions are made for assigning a unique identifier. Similarly, recordation of the location of samples at block 708 may precede, or occur simultaneously with, transfer of specimen material to discrete sample nodes at block 706 in certain situations.

FIG. 8 is a simplified flow diagram illustrating one embodiment of a method of retrieving and preparing an archive sample for analysis. As indicated at block 801, the archive sample retrieval process in an exemplary embodiment may generally begin with receipt of a request. A medical researcher or technician, for instance, may request retrieval of blood or DNA samples. Such requests may be transmitted from remote network clients across a communication network. In situations where a researcher is interested in a specific disease or a specific type of analysis, the request may be related to, or include relevant information with respect to, a particular type of experiment or analysis, for example.

In an embodiment such as depicted and described above with reference to FIGS. 1–3, for example, a researcher at a remote network client location may transmit a request to an archive facility via a network. Remote inquiries may seek to ascertain the availability of samples which may be appropriate for the intended experimentation, and may include requests for access to data records or other clinical information related to samples and sample sources; as noted above, such data records may be maintained in one or more data structures at the archive facility. Through Boolean search queries, for example, or other data searching techniques which are generally known in the art, one or more suitable samples may be identified responsive to the request; suitability of particular samples may be based upon relevant clinical data and history. Sample identification is generally depicted at block 802, and may be facilitated by random sample selection from designated or specified sample categories or sample types. Accordingly, broad categories containing many samples, all of which satisfy selected criteria, may be narrowed automatically through random selection of particular samples within the defined categories.

In some embodiments, a purchase order specifying some or all of the identified samples may be submitted, followed by a request that the samples be prepared for shipment to a remote location; additionally or alternatively, a researcher may request that certain analyses, experiments, or portions thereof be performed using the identified samples at the archive facility. In any event, a sample carrier supporting the identified sample may be located in the archive facility (block 803). As described in detail above, location and retrieval of particular sample carriers may be facilitated by unique identifying indicia disposed on each sample carrier in the archive facility; robotics and machine vision or bar code reader technology may enable automatic location and retrieval of sample carriers. Alternatively, a technician or administrator at the archive facility may locate and retrieve one or more sample carriers at block 803 manually.

As indicated at block 804, preparation of a sample for analysis may involve detecting a location of a discrete sample node on the retrieved sample carrier; as set forth above with reference to the sample carriers illustrated in FIGS. 4 and 5, structural arrays and sample structures may support a plurality of discrete sample nodes in a predetermined spatial relationship relative to each other and relative to a sample container such as a test tube or a particular well of a multi-well plate. As sample nodes are removed from a particular sample carrier during its useful life, the efficient detection of sample structures to which sample nodes are still attached may increase overall system throughput. As noted above, detecting the location of a sample node on a sample carrier may be facilitated by, inter alia, data records related to previous sample removal operations, machine vision or optical technology, or operator-assisted positioning tools for robotic sample removal mechanisms.

Following detection or location, discrete sample nodes may be removed from the sample carrier as indicated at block 805. Removal of sample nodes may be performed with optical equipment as illustrated in FIG. 5C; as described above, the FIG. 5C embodiment may virtually eliminate risks of cross contamination due to material transferred from one sample node to the next by a mechanical sample removal tool or device. Specifically, the FIG. 5C embodiment may employ a laser coupled to a precise positioning system; lased, coherent light may sever the sample structure supporting the sample node, depositing the sample node into a sample container for future processing.

Alternatively, the mechanical clipper (FIG. 5D) or equivalent cutting devices may be employed for sample removal at block 805; in an embodiment utilizing a mechanical sample node removal tool, the tool may be constructed and operative to make contact only with the sample structure supporting the sample node to be removed. Accordingly, cross contamination between samples may be avoided, since the sample node removal device does not make contact with any sample material.

At decision block 806, a determination may be made with respect to shipping the samples. Where a request for shipment has been made by the researcher, for example, the sample container into which the sample node has been deposited may be sealed and packaged for shipment; as indicated at block 807, samples may be purified with one or more appropriate procedures prior to shipment such that, upon arrival at a remote location, the samples may be in condition for immediate experimentation (block 899). By way of specific example, a PCR amplification may precede shipment; the DNA attached to the sample support medium at the sample node may serve as the DNA template, and PCR reagents may then be deposited directly into the sample container.

Where shipping has not been requested, or where analysis is requested prior to shipment, processing may proceed in accordance with the request as indicated at block 808. Various testing, experimentation, and analysis may be conducted at the archive facility or at a remote facility as set forth in detail above. Test results, data, or other relevant information may be recorded as indicated at block 809; additionally or alternatively, the acquired data may be transmitted, either responsive to a specific request or automatically, for example, to a researcher at a remote location via a network connection as described above with reference to FIGS. 1–3.

Those of skill in the art will appreciate that the FIG. 8 embodiment is provided by way of example only, and that various alternatives exist. In an embodiment accommodating both processing at an archive facility as well as shipment of samples to a remote site, for example, the operations indicated at blocks 807 and 899 may follow recordation and transmission of experimental results at block 809. As another alternative, the determination at decision block 806 may directly follow reception of a request (block 801) or sample identification (block 802); it is possible in this embodiment, for example, that an entire sample carrier may simply be shipped directly to a remote location without sample node detection, removal, or analysis.

In addition to sample archival and retrieval, myriad DNA analysis services may be provided to remote clients in conjunction with affiliated genomics companies. For example, researchers may be primarily interested in the genotypes of specific patient or sample classes as opposed to the samples themselves. In this situation, remote clients may specify not only specific samples or sample categories of interest, but also particular genes or gene sequences of interest. An affiliated company, for example, under contract with the archive facility, may design a custom DNA chip used to genotype the selected samples; accordingly, genotyping results may be transmitted electronically (via a secure or encrypted network connection, for example) to a remote client. Since the sample nodes may be delivered in standard microtiter plates as set forth above, samples may be delivered in suitable condition for immediate amplification for subsequent desired experimentation or analysis.

The embodiments described above are scalable; as numerous archive facilities are employed and networked, a vast database of samples and information related to sample sources may be statistically mined to reveal DNA-directed therapeutics and, ultimately, cures for many genetic ailments.

The present invention has been illustrated and described in detail with reference to particular embodiments by way of example only, and not by way of limitation. Those of skill in the art will appreciate that various modifications to the disclosed embodiments are within the scope and contemplation of the invention. Therefore, it is intended that the invention be considered as limited only by the scope of the appended claims.

What is claimed is:

1. A method of preparing an archive sample for analysis; said method comprising:
    identifying a sample to be analyzed;
    responsive to said identifying, ascertaining a location of said sample on a discrete sample node supported by a sample carrier; said discrete sample node comprising a sample support medium operative to carry a discrete sample in desiccated form;
    responsive to said ascertaining, removing said discrete sample node from said sample carrier; and
    preparing said sample for analysis, wherein said sample is biological, and wherein said sample is a polynucleotide.

2. The method of claim 1 wherein said identifying comprises interrogating a data structure.

3. The method of claim 1 wherein said ascertaining comprises utilizing an optical sensor.

4. The method of claim 1 wherein said ascertaining comprises reading a bar code.

5. The method of claim 1 wherein said ascertaining comprises identifying a unique signal transmitted from a transceiver attached to said discrete sample node.

6. The method of claim 5 wherein said removing comprises transmitting a control signal to said transceiver.

7. The method of claim 1 wherein said removing comprises utilizing a laser.

8. The method of claim 1 wherein said removing comprises utilizing a mechanical clipping tool.

9. The method of claim 1 wherein said preparing comprises depositing said discrete sample node in a sample container.

10. The method of claim 1 wherein said preparing comprises washing sample material attached to said discrete sample node.

11. The method of claim 1 wherein said preparing comprises amplifying said polynucleotide.

12. A method of preparing an archive sample for analysis; said method comprising:
   receiving a request related to an experiment;
   identifying a sample suitable for said experiment;
   responsive to said receiving and said identifying, locating a sample carrier supporting said sample on a discrete sample node; said discrete sample node comprising a sample support medium operative to carry a discrete sample in desiccated form;
   detecting a location of said discrete sample node on said sample carrier;
   removing said discrete sample node from said sample carrier; and
   preparing said sample for analysis, wherein said detecting comprises obtaining video signals output from an optical sensor.

13. The method of claim 12 wherein said locating comprises interrogating a database maintaining records related to said sample carrier.

14. The method of claim 12 wherein said locating comprises utilizing an optical sensor.

15. The method of claim 12 wherein said locating comprises reading a bar code.

16. The method of claim 12 wherein said removing comprises automatically operating a sample node removal device responsive to said obtaining video signals.

17. The method of claim 12 wherein said removing comprises manually operating a sample node removal device.

18. The method of claim 12 wherein said removing comprises utilizing a laser.

19. The method of claim 12 wherein said removing comprises utilizing a mechanical clipping tool.

20. The method of claim 12 wherein said preparing comprises depositing said discrete sample node in a sample container.

21. The method of claim 12 wherein said preparing comprises washing sample material attached to said discrete sample node.

22. The method of claim 12 wherein said sample is non-biological.

23. The method of claim 12 wherein said sample is biological.

24. A method of preparing an archive sample for analysis; said method comprising:
   receiving a request related to an experiment;
   identifying a sample suitable for said experiment;
   responsive to said receiving and said identifying, locating a sample carrier supporting said sample on a discrete sample node; said discrete sample node comprising a sample support medium operative to carry a discrete sample in desiccated form;
   detecting a location of said discrete sample node on said sample carrier;
   removing said discrete sample node from said sample carrier; and
   preparing said sample for analysis, wherein said sample is biological, and wherein said sample is a polynucleotide.

25. The method of claim 24 wherein said preparing comprises amplifying said polynucleotide.

26. A method of preparing an archive sample for analysis; said method comprising:
   identifying a sample to be analyzed; said sample maintained in desiccated form and carried on a sample support medium associated with a discrete sample node;
   responsive to said identifying, obtaining said sample;
   preparing said sample for analysis; and
   selectively repeating said identifying, said obtaining, and said preparing at a rate sufficient to prepare in excess of 100 samples for analysis per day wherein said sample is biological, and wherein said sample is a polynucleotide.

27. The method of claim 26 wherein said identifying comprises interrogating a database.

28. The method of claim 26 wherein said identifying comprises utilizing an optical sensor.

29. The method of claim 26 wherein said obtaining comprises automatically operating a sample node removal device.

30. The method of claim 29 wherein said obtaining comprises utilizing a laser.

31. The method of claim 29 wherein said obtaining comprises utilizing a mechanical clipping tool.

32. The method of claim 26 wherein said preparing comprises depositing said sample in a sample container.

33. The method of claim 26 wherein said preparing comprises washing said sample.

34. The method of claim 26 wherein said preparing comprises amplifying said polynucleotide.

35. The method of claim 26 wherein said selectively repeating occurs at a rate sufficient to prepare in excess of 200 samples for analysis per day.

36. The method of claim 26 wherein said selectively repeating occurs at a rate sufficient to prepare in excess of 500 samples for analysis per day.

* * * * *